United States Patent [19]
Payne et al.

[11] Patent Number: 5,340,483
[45] Date of Patent: Aug. 23, 1994

[54] TWO STEP PROCESS FOR CONVERSION OF A WEAKLY ADSORBABLE COMPOUND TO A STRONGLY ADSORBABLE COMPOUND AND SELECTIVE REMOVAL THEREOF

[75] Inventors: Gregory F. Payne, Hunt Valley; Jennifer Chu, Bowie; Kimberlee K. Wallace, Jessup; Wei-Qiang Sun, Lutherville, all of Md.

[73] Assignee: University of Maryland at College Park, College Park, Md.

[21] Appl. No.: 75,283

[22] Filed: Jun. 11, 1993

[51] Int. Cl.$^5$ .................. C02F 1/28; B01D 15/00
[52] U.S. Cl. .................. 210/632; 210/668; 210/669; 210/909; 435/43; 435/262; 526/77; 568/628; 568/630
[58] Field of Search ............... 210/668, 669, 632, 909; 435/43, 262; 526/77; 568/628, 630

[56] References Cited

U.S. PATENT DOCUMENTS

| | | | |
|---|---|---|---|
| 3,671,552 | 6/1972 | LeBris et al. | 260/369 |
| 3,678,081 | 7/1972 | Crivello | 260/396 |
| 3,740,315 | 6/1973 | Li et al. | 195/2 |
| 4,026,791 | 5/1977 | Wallace | 210/21 |
| 4,072,671 | 2/1978 | Sodini et al. | 260/123.5 |
| 4,164,469 | 8/1979 | Wagner | 210/40 |
| 4,177,139 | 12/1979 | Hahn et al. | 210/33 |
| 4,360,469 | 11/1982 | Dietl et al. | 260/396 |
| 4,420,397 | 12/1983 | Kaneko et al. | 435/262 |
| 4,420,643 | 12/1983 | Savides et al. | 568/753 |
| 4,485,016 | 11/1984 | Hopkins | 435/262 |
| 4,505,821 | 3/1985 | Kaneko et al. | 435/262 |
| 4,575,568 | 3/1986 | Yuhas, Jr. et al. | 568/749 |
| 4,765,901 | 8/1988 | Field | 435/262 |
| 4,820,420 | 4/1989 | Hums et al. | 210/669 |
| 4,827,049 | 5/1989 | Zinnen | 568/753 |
| 4,980,065 | 12/1990 | Hsu | 210/632 |
| 5,039,414 | 8/1991 | Muller et al. | 210/632 |
| 5,051,184 | 9/1991 | Taylor | 210/632 |
| 5,078,886 | 1/1992 | Hsu | 210/632 |
| 5,169,535 | 12/1992 | Adachi et al. | 210/669 |
| 5,178,762 | 1/1993 | Pokora et al. | 210/632 |

FOREIGN PATENT DOCUMENTS

| | | | |
|---|---|---|---|
| 914507 | 3/1982 | U.S.S.R. | 210/632 |
| 914508 | 3/1982 | U.S.S.R. | 210/632 |
| 939407 | 6/1982 | U.S.S.R. | 210/623 |

OTHER PUBLICATIONS

"Covalent Binding of Aromatic Amines to Humates. 1. Reactions with Carbonyls and Quinones", George E. Paris, *Environmental Science & Technology*, vol. 14, No. 9, Sep. 1980, pp. 1099–1106.

"Melanoproteins 1. Reactions Between Enzyme-generated Quinones and Amino Acids", H. S. Mason et al, *Biochem. Biophys. Acta*, 111, (1965) pp. 134–146.

"Quinone-amine polymers: 10. Use of calcium Hypochlorite in the Syntheses of Polyamine-Quinone (PAQ) Polymers", V. S. Nithianandam et al, *Polymer*, 1991, vol. 32, No. 6, pp. 1146–1149.

"Quinone–Amine Polymers. II. 1,3–Bis(3–Aminophenoxy)benzene–p–Benzoquinone Oligomers", *Journal of Polymer Science: Part A: Polymer Chemistry*, vol. 27, 865–871 (1989).

"Metal Recovery Using Chitosan", Edvar Onsoyen et al, *J. Chem. Tech. Biotechnol.*, 1990, 49, pp. 395–404.

Primary Examiner—Neil McCarthy
Attorney, Agent, or Firm—Burns, Doane, Swecker & Mathis

[57] ABSTRACT

A method for the selective separation of a particular compound from a mixture of compounds, by enzymatically converting a weakly adsorbable compound to a strongly adsorbable compound, and binding the converted compound to a material of appropriate chemical properties is described. Also described are methods for removing contaminants from wastewater streams, and from intermediate chemical process streams.

20 Claims, 13 Drawing Sheets

TWO STEP PROCESS FOR CONVERSION OF A WEAKLY ADSORBABLE COMPOUND TO A STRONGLY ADSORBABLE COMPOUND AND SELECTIVE REMOVAL THEREOF

This invention was made with Government support under CTS-8912141 awarded by NSF. The Government has certain rights in the invention.

FIELD OF THE INVENTION

The present invention relates to a two-step process for the enzymatic conversion of a weakly adsorbable compound to a strongly adsorbable compound, and its selective adsorption to a material with the appropriate chemistry. The present invention further relates to a process for the selective separation of phenolic impurities from intermediate manufacturing wastewater streams, wherein 1) the phenols and phenolic derivative impurities in a wastewater stream are enzymatically oxidized to quinones, and 2) the quinones are selectively separated by chemisorption. This coupled approach can be referred to as tyrosinase reaction/chitosan adsorption (TR/CA).

BACKGROUND OF THE INVENTION

In the past, compounds have been selectively adsorbed from solutions by taking advantage of their affinity for a particular substrate. Generally, it has been recognized as an advantage to weakly adsorb a compound to a substrate so that the binding can be subsequently reversed.

It is often desired to selectively remove particular classes of synthetic industrial chemicals from manufacturing streams, as they are common components of wastewater, and can be observed as groundwater contaminants. Phenols represent one of the most important such classes of synthetic industrial chemicals and are often observed in effluents from various manufacturing or industrial operations, such as the manufacture of aniline, cumene-phenol processes, petroleum refining, petrochemical manufacture, coal gasification and coal liquification processes. Moreover, phenols are common components of pulp and paper wastes and have been observed as groundwater contaminants. However, despite the importance of treating phenol-containing wastewaters, current methods are not satisfactory and the search for improved methods continues.

Depending upon the process and the phenol concentration of the waste water, the aim is to recover the phenolic impurities and to reduce the level of phenols in the waste water to a negligible degree. In most cases, however, a recovery of the phenols is not practical since the expense of such recovery renders a process in which recovery is contemplated relatively impractical. Furthermore, the cost for the phenol recovery from solvents or adsorbents is often excessive.

Existing methods for removal of aromatics from aqueous solution typically comprise physical adsorption onto various media having a high surface activity, including active carbon, silica gel and synthetic-resin exchangers, metabolism by various microorganisms and chemical combustion in the presence of various oxidants. Alternatively, phenols can be removed by extraction or scrubbing with selective organic solvents or by steam distillation.

Unfortunately however, each of these methods has some or all of the following drawbacks: (a) time consuming, (b) expensive, (c) ineffective in dealing with pollutants at the levels encountered and/or in reducing pollutant levels to those desired, (d) exhibit a temperature sensitivity which can result in large seasonal variations, and (e) have a narrow specificity with respect to the classes of aromatic compounds amenable to treatment. Moreover, physical and chemical treatment methods become exceedingly expensive when a low effluent concentration must be achieved.

In the adsorption process, practical considerations have limited the adsorbent to active carbon. An adsorption process for the removal of phenols from waste waters, using active carbons, has various problems associated with it. For example, nonphenolic constituents of the wastewater are deposited on the active carbon which cannot be readily removed. Such materials include resinous and asphalt-type materials. In addition, the desorption or regeneration processes have a tendency to produce resinous and asphalt-type materials which are not completely released or destroyed by the active carbon so that the active carbon must often be replaced.

However, in many wastewater treatment applications, the activated carbon requirements have dramatically increased due to the need to meet more stringent effluent standards. Thus, although the activated carbon adsorption process is economically disadvantageous and the carbon particles have limited reusability, a treatment of the active carbon for reuse is practically mandated by the high cost of the adsorbent.

Chitosan, a polyglucosamine derived from chitin, has been shown to be effective as an adsorbent. Chitin can be obtained from sources such as crustacean shells, and other animal and fungal by-products, and can be converted to chitosan by deacetylation. Methods for obtaining chitosan are described in U.S. Pat. Nos. 4,282,351, 4,368,322 and 4,835,265.

Portier, in U.S. Pat. Nos. 4,882,066 and 4,775,650, describes compositions and processes for removal of metals contaminants or halogenated organic compounds from liquid streams polluted with these materials. The compositions are characterized as porous solids on the surfaces of which thin films of chitinous material are dispersed.

Microbiological dephenolation approaches have shown great promise for treating phenolic wastes (e.g., see Donaldson et al., *Environ. Prog.* 1987, vol. 6, pp. 205–211, and Worden and Donaldson, *Biotechnol. Bioeng.* 1987 vol. 30, pp. 398–412). For example, it is known to dephenolate waste waters by biological degradation of the phenolic impurities in synthetic biological environments and installations. However, for small volume wastes which are generated discontinuously, microbiological treatment has been plagued by instabilities resulting from the toxicity of these compounds to the microbial population (Jones et al., *J. Gen. Microbiol.* 1973 vol. 74, pp. 139–148; Yang and Humphrey, *Biotechnol. Bioeng.* 1975 vol. 17, pp. 1211–1235).

The idea of using enzymes for treating phenol-containing wastewaters was first proposed in the 1980s. Early workers suggested that enzymes could be used to convert soluble phenols and anilines present in wastewater into insoluble and apparently non-toxic polyphenolic precipitates which could be removed by filtration. Enzymes considered for this phenol precipitation included peroxidases (Klibanov and Morris, *Enzyme Microb. Technol.* 1981 vol. 3, pp. 119–122; Klibanov et al., *J. Appl. Biochem.* 1980 vol. 2, pp. 414–421, *Science* 1983 vol. 221, pp. 259–261; Aitken et al., *Water Res.* 1989 vol. 23, p. 443), laccases (Shuttleworth and Bollag, *Enzyme Microb. Technol.* 1986 vol. 8, pp. 171–177) and tyrosinases (Allow et al., *Biotechnol. Bioeng.* 1984) vol. 26, pp. 599–603. Advantageously, enzymes can react with a wide range of phenols even under dilute conditions and that these enzymes are likely to be less sensitive to operational upsets than microbial populations.

However, treatment of wastewater by the addition of peroxidase and hydrogen peroxide, although effective for its intended purpose, was found to have serious shortcomings which precluded it from being commercially attractive. In particular, hydrogen peroxide is expensive, unstable on storage and short lived in a real waste stream situation where metal salts, sunlight, and bacteria rapidly degrade the peroxides to oxygen and water. As a result, others have attempted to capture the advantages of enzymatic oxidation of the phenolic impurities in wastestreams, while overcoming the disadvantages.

For example, in U.S. Pat. No. 4,485,016, Hopkins teaches the removal of at least one organic compound, including aromatic hydroxy compounds, aromatic amines and phenols, from contaminated waste water. By this process the wastewater is treated with a treatment agent consisting essentially of peroxidase, an enzymatic agent consisting of alcohol oxidase and a straight chain $C_1$ to $C_4$ alcohol or glucose oxidase and glucose, and an azide salt, followed by separation of the precipitate by standard physical means, e.g., filtration, centrifugation, sedimentation, and the like.

In U.S. Pat. No. 4,623,465, Klibanov claims a process in which an oxidative enzyme, peroxidase, is added to the aqueous solution to be treated along with the enzyme's co-substrate, hydrogen peroxide. This mixture converts susceptible aromatic compounds to radicals which in a subsequent, presumably non-enzymatic, step couple with one another to eventually aggregate into a precipitate. Susceptible aromatics are hydroxy- and amino-substituted compounds with various other substituents such as alkyl, alkoxy, halo and fused aryl. In particular, Klibanov teaches the specific use of horseradish peroxidase for the oxidation of phenols to form a filterable precipitate.

Peroxidases are enzymes that catalyze chemical reactions that normally involve the transfer of hydrogen radicals from organic substances to substrates comprising peroxides. Such reactions may be complex, and may involve many different substances. Theoretically, the horseradish peroxidase reacts with phenol by removing a hydrogen radical (one proton with one electron) from the hydroxide group on the phenol. Thus, the phenol is thereby converted to an aromatic free radical, which participates in a subsequent reaction that depends upon other substances that are present in the solution, while the hydrogen radical reacts with hydrogen peroxide to form water.

The findings are also described in a series of publications and reports from Klibanov and co-workers, including: (1) *Science* 221:259–261 (1983); (2) Klibanov, National Technical Information Service, PB84–138155, 1–18 (1983); (3) Detoxification Hazard Waste (Symp., 1981), Edited by J. H. Exner, Ann Arbor Sci., CA 98(12):95130c (1982); (4) Atlow et al., *Biotechnology and Bioengineering*, XXVI:599–603 (1984); (5) Klibanov et al., *Enzyme and Microbiol. Technol.* 3(2): 119–22 (1981); (6) Klibanov, *Enzyme Engineering* 6, 3(2):319–325 (1982); and (7) Klibanov et al., *Journal of Applied Biochemistry* 2:414–421 (1980).

The specific improvement claimed by Klibanov is the ability of such a system to effect the clearance of compounds which are not substrates of the enzyme as long as there is a good substrate (a hydroxy- or amino-aromatic compound) also present. Thus, the clearance of a poor substrate is augmented in the presence of a good substrate. There are, however, aspects to this approach which lower its economic feasibility: (a) it requires large amounts of enzyme because the enzyme appears to be progressively inactivated under the reaction conditions; (b) relatively high concentrations of hydrogen peroxide are employed which are themselves inhibitory to the enzyme; (c) the treatment requires 3 to 24 hours for completion; (d) a final filtration or centrifugation step is required to remove the precipitate generated; and (e) each of the pure compounds studied appears to require removal at a different pH.

In U.S. Pat. No. 4,765,901, Field teaches a process for treating waste water by subjecting the contaminating phenolic compositions to oxidative treatment, specifically by polyphenoloxidase enzymes, to increase the phenolic polymerization into polyphenolic aggregates for physical removal, e.g., precipitation, filtration or the like. The process is defined as oxidative detoxification as opposed to oxidative dephenolization. Thus, the primary purpose of the process is a pretreatment to convert phenolic compounds into a harmless form, not a process of purification.

Field determined that waste water contaminated by phenolic impurities can be purified anaerobically in an excellent manner if, prior to the anaerobic purification, the waste water is subjected to an oxidative treatment. The oxidative treatment serves to increase the phenolic degree of polymerization, the formation of larger polymers from the smaller phenolic compounds originally present reducing or eliminating the methanogenic toxicity of the phenolic compounds originally present. Thus, Field teaches that the degree of polymerization, and consequently the toxicity to methanogenic bacteria, can therefore be influenced by an oxidative pretreatment.

In U.S. Pat. No. 5,051,184, Taylor claims the removal from aqueous solution of aromatic compounds, specifically including phenols, using an oxidative enzyme which is immobilized on a solid surface. Taylor teaches that the inhibitory action of elevated hydrogen peroxide concentration in batch processes is obviated by carrying out the clearance process at substoichiometric concentrations of peroxide in a flowing stream. The peroxide is continuously added to the mixture and collection and removal of the precipitate is accomplished by allowing the precipitate to accumulate on the filter on which the enzyme is immobilized.

However, there appear to be three rather serious problems involved in the methods for the enzymatic precipitation of phenols from wastewaters. These problems become apparent in light of the enzymatic and subsequent nonenzymatic reactions which occur in the presence of tyrosinase:

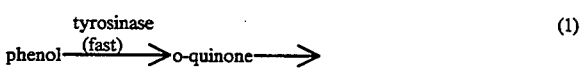  (1)

-continued

Quinones are rapidly formed from the tyrosinase-catalyzed oxidation of phenols. These quirtones are reactive and undergo nonenzymatic conversion to form additional, more stable intermediates. The more stable intermediates slowly undergo oligomerization reactions which ultimately can yield high molecular weight, insoluble polyphenolics.

The first problem with the enzymatic phenol precipitation approach is that the oligomerization and precipitation reactions are generally slow, requiring hours to days for completion. Secondly, unless initial phenol concentrations are very high, oligomerization may be limited to the formation of low molecular weight oligomers, which remain in solution rather than precipitating. Finally, the enzymes can be inactivated by the reactive intermediates generated from their reactions (Atlow et al., *Biotechnol. Bioeng.* 1984 vol. 26, pp. 599–603; Canovas et al., *Biochem. Biophys. Acta* 1987 vol. 912, pp. 417–423). Thus, despite the advantageous fact that the enzymes can react with a range of phenolics, even under dilute conditions, the previously-proposed approach of using enzymes for phenol precipitation has serious practical limitations.

Thus, there has been a long felt need in the art for a reliable, efficient and economical method for the selective separation of phenolic impurities from a wastestream which is not hampered by the above mentioned limitations. It is precisely this long-felt need which the present inventive two-step process for the selective separation of phenols from a wastestream was designed to meet.

SUMMARY OF THE INVENTION

The present invention relates to a two-step process for the selective conversion of a particular chemical compound from a mixture of compounds, by utilizing an enzyme to convert the particular chemical compound, which is weakly adsorbable, to a strongly adsorbable compound. The strongly adsorbable compound is then adsorbed to a material of appropriate chemistry, such that it can be selectively and efficiently removed from the mixture.

The present invention also relates to a two-step process for the selective removal of phenolic impurities from mixtures containing nonphenolic isomers, such as wastewaters. By using the enzyme tyrosinase, it is possible to convert weakly adsorbable phenols and phenolic impurities into reactive intermediates (quinones) which can be strongly adsorbed onto sorbents of appropriate surface chemistries.

An object of the present invention is to provide a two-step process for the selective removal of a weakly adsorbable compound from a mixture of compounds by:

a) enzymatically converting the weakly adsorbable compound to a strongly adsorbable compound; and b) adsorbing the strongly adsorbable compound to a material of the appropriate chemistry to selectively remove the strongly adsorbable compound from the mixture.

Another object of the present invention is to provide a method for the selective removal of a phenolic contaminant from complex mixtures, by:

(a) oxidizing the contaminant with an enzyme specific for the contaminant; and (b) binding the oxidized contaminant to a sorbent.

Another object of the present invention is to provide a method for removing a contaminant from a recycle stream by:

a) oxidizing the contaminant with an oxidizing enzyme specific for the contaminant; and b) binding the oxidized contaminant to a sorbent.

Yet another object of the present invention is to provide a method of improving the manufacturing efficiency of a polymer by:

a) enzymatically convening a polymerization-inhibiting compound present in a solution of monomers to a strongly adsorbable compound; and b) adsorbing the strongly adsorbable compound to a material of the appropriate chemistry to selectively remove the strongly adsorbable compound from said mixture.

Additional objects, advantages and novel features of the invention will be set forth in part in the description which follows, and in part will become apparent to those skilled in the art on examination of the following description, or may be learned by practice of the invention.

DESCRIPTION OF THE PREFERRED EMBODIMENTS

Figure 1:
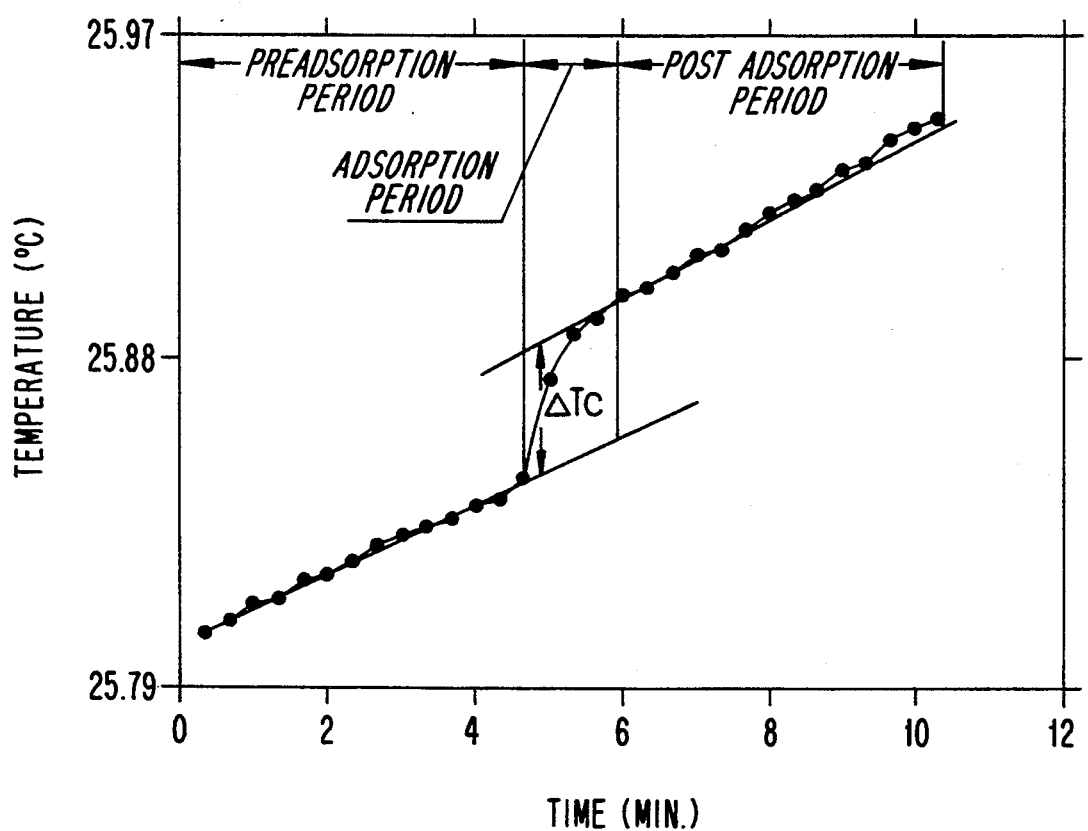
FIG. 1 is a typical thermogram used to determine the temperature rise ($\Delta T_c$) for adsorption.

The invention relates to any two-step process wherein an enzyme converts a weakly adsorbable compound to a strongly adsorbable compound which is then adsorbed by a material with the appropriate chemistry to efficiently adsorb the compound. One particular embodiment is the method of TR/CA.

There are two unique features of TR/CA which can be exploited for waste minimization. First, the substrate specificity of tyrosinase confers selectivity to TR/CA. The second unique feature of TR/CA is that due to the strength of quinone-chitosan binding, phenols can be efficiently removed from solution. The importance of strong binding is that the adsorption affinity, or the ability of a sorbent to remove trace levels of a contaminant, is exponentially related to the adsorption enthalpy.

Because high separation factors can be achieved by tyrosinase-containing chitosan gels, multiple-staged contacting is not needed and thus the following advantages can be readily envisioned:

(i) Since staged contacting is not necessary, TR/CA does not require the capital-intensive equipment characteristic of most separations (e.g. distillation).

(ii) The high separation factors make TR/CA simple to implement (e.g. as contrasted to the operational complexity of swing adsorption processes).

(iii) TR/CA should result in the generation of less waste compared to competing extraction or chromatographic techniques which result in the generation of considerable amounts of waste solvent (either the extracting or eluting solvent).

To illustrate the simplicity of using TR/CA, consider the addition of tyrosinase-containing chitosan gels directly to a storage tank to eliminate a contaminating phenol, just as a drying agent (e.g. molecular sieve or magnesium sulfate) would be added to eliminate water from nonaqueous solvents. Thus the low capital cost and simplicity of utilizing TR/CA would allow specialty and commodity chemical producers to implement waste minimization strategies even for small batches with short turn-around times.

In summary, because of the substrate specificity of tyrosinase and the strength of quinone-chitosan binding, TR/CA offers selective and efficient removal of contaminating phenols from process streams. With respect to separations, this high selectivity and efficiency translates into very large separation factors which eliminates the need for multiple equilibrium staged contacting.

In this embodiment of the present invention, tyrosinase is used to generate reactive intermediates, which are then strongly adsorbed onto specific sorbents. This approach is illustrated by the following:

Step 1: Tyrosinase Reaction $$\text{phenol} \rightarrow \text{o-quinone} + \text{other intermediates} \quad (2)$$

Tyrosinases are enzymes capable of oxidizing phenols to quinones using molecular oxygen. This enzyme oxidation proceeds without the need for complex externally added cofactors.

A potential benefit of using tyrosinase in the two-step approach is that tyrosinase can react with a range of phenolics and is less sensitive to changes in waste stream composition and strength (Atlow et al., *Biotechnol. Bioeng.* 1984 vol. 26, pp. 599–603). Therefore, this enzymatic approach is likely to be more generic and operationally stable than microbiological treatment approaches. Microbiological treatment of phenolic wastes is plagued by instabilities resulting from the toxicity of these compounds to the microbial population (Jones et al., *J. Gen. Microbiol.* 1973 vol. 74, pp. 139–148; Yang and Humphrey, *Biotechnol. Bioeng.* 1975 vol. 17, pp. 1211–1235). Although laboratory studies have demonstrated considerable benefit for the steady-state operation of microbial reactors, there are often problems in attaining and maintaining steady states in applications where the wastes are generated discontinuously and where the waste strength and composition varies over time. Further, the ability of using tyrosinase on an "as needed basis" provides the flexibility of treating small-scale and/or urgent waste problems (e.g., accidental discharges) without the need for adapting a microbial culture to the waste.

In the second step of this two-step approach, the reactive intermediate generated from the tyrosinase-catalyzed oxidation (i.e., the quinone) is adsorbed. The key to this treatment approach is that the sorbent must be readily available and effective.

Step 2: Chemisorption $$\text{o-quinone} + \text{other intermediates} + \text{sorbent} \rightarrow \text{chemisorbed compounds} \quad (3)$$

The polyglucosamine chitosan, which is derived from chitin may be used as a reactive sorbent. Chitin is an abundant natural polymer which is a readily available waste product. There is considerable interest in developing chitosanbased products because geographic areas with large shellfish industries are experiencing considerable problems disposing of the overabundant, chitin-rich shells.

The rationale for using chitosan as a sorbent is not merely that chitosan is a waste material, but rather that there are specific chemical reactions between chitosan and the tyrosinase-generated quinones which can be exploited to strongly adsorb these compounds. It appears that the amine in the chitosan structure reacts with compounds containing carbonyl groups to form covalent bonds (Milun, *Anal. Chem.* 1957 vol. 29, pp. 1502–1504; Hall and Yalpani, *J. Chem. Soc., Chem. Commun.* 1980, pp. 1153–1154; Muzzarelli et al., *Carbohydr. Res.* 1982 vol. 107, pp. 199–214). In a study involving the binding of amines to carbonyl-and quinone-containing organics, Parris (1980) suggested that two reaction paths are possible, a rapid reversible reaction resulting in imine formation and an irreversible oxidative reaction path resulting in the formation of aminoquinones.

Because adsorption of quinones onto chitosan is very strong, the twostep approach is highly effective for removing traces of phenols from wastewaters. The importance of adsorption strength is illustrated by the proportionality:

$$\text{affinity} \propto e^{-\Delta H^\circ/RT} \quad (4)$$

where the adsorption affinity is shown to increase exponentially with increases in the adsorption strength (i.e., $\Delta H^\circ$) (Maity et al. *Ind. Eng. Chem. Res.*, 1991 vol. 30, pp. 2456–2463). An increased adsorption affinity is particularly important because increasingly stringent effluent standards mandate that phenols be removed from more dilute wastewaters. Enthalpies of $-24.7$ kcal/mol for chitosan and $-7$ kcal/mol for activated charcoal adsorption can be observed. For an order of magnitude comparison, if we assume the proportionality in relation 4 is similar for chitosan and activated charcoal adsorption, then $$\frac{(\text{affinity})_{chit}}{(\text{affinity})_{char}} = e^{-(\Delta H_{chit}^\circ - \Delta H_{char}^\circ)/RT} \quad (5)$$

From the above equation and the measured 17 kcal/mol enthalpy difference, chitosan adsorption can be estimated to yield a $10^{12}$-fold improvement in adsorption affinity over activated charcoal. This estimate illustrates that the two-step tyrosinase reaction/chitosan adsorption approach offers significant potential advantages for removing traces of phenols from wastewaters.

Another potential benefit of the two-step tyrosinase reaction/chitosan adsorption is that chitosan is obtained from chitin, a waste product of the shellfish industry. In many places, the chitin-rich wastes from this industry are landfilled at considerable cost. Thus, the tyrosinase reaction/chitosan adsorption approach provides a potential opportunity to convert this waste into a useful product.

The aromatic compounds which can be removed by the present invention, particularly include aromatic amines and hydroxides. Examples are:

| | |
|---|---|
| phenol | 4-chlorophenol |
| 2-chlorophenol | 4,4'-dihydroxybiphenyl |
| 2,2'-dihydroxybiphenyl | 2-aminophenol |
| 8-hydroxyquinoline | 3-cresol |
| 3-aminophenol | 2,6'dimethylphenol |
| 2-cresol | 3-methoxyphenol |
| 4-cresol | 2-methylphenol |
| 2,3-dimethylphenol | 1-naphthol |
| 2-methoxyphenol | 4-phenylphenol |
| 4-methoxyphenol | p-hydroxyphenoxyacetic acid |
| resorcinol | 5-methylresorcinol |
| 1-nitrosonaphthol | tert-butylcatechol |
| hydroquinone | |

The enzymes which can be used include peroxidases, haloperoxidases, lactoperoxidase, ligninases (manganese-dependent or-independent), tyrosinase (also known as polyphenol oxidase) and cytochromes as well as heine proteins such as hemoglobin and the like. Some of the enzymes use oxygen directly as a substrate (e.g. tyrosinase) while others use alternative substrates (e.g., hydrogen peroxide). All are regarded as "oxidative" enzymes. Equivalent results can be achieved where oxygen is dissolved in the aqueous solution for oxidative enzymes.

Where an enzyme other than a tyrosinase is employed, reactants other than phenols may be utilized, and products other than quinones will be produced. For example, where peroxidases are employed, free radicals will be produced. For products other than quinones, adsorbants other than chitosan may be required.

The oxidative substrates for the oxidative enzymes include oxygen, hydrogen peroxide, various alkyl hydroperoxides such as methyl hydroperoxide and/or percarboxylic acids such as peracetic acid and the like.

The present invention can also be used to remove a contaminant and therefore facilitate the recycling of a reusable "precursor" in an antibiotic manufacturing operation. A preferred precursor is phenoxyacetic acid which is used in the manufacture of semisynthetic $\beta$-lactams derived from penicillin V.

In the manufacture of penicillin V, the precursor phenoxyacetic acid is fed to the fermentation to direct biosynthesis (for review see Hersbach, et al, *Biotechnology of Industrial Antibiotics*, pp. 45–140 (1984). Although some penicillin V is used directly as a therapeutic, much of the penicillin V produced is modified to produce semisynthetic $\beta$-lactams. A common step for many semisynthetic penicillins is deacylation, in which the penicillin V is chemically or enzymatically hydrolyzed, to yield 6-aminopenicillanic acid and to regenerate the phenoxyacetic acid precursor. Because the phenoxyacetic acid represents a significant fraction of the fermentation raw materials (both in terms of mass and cost), it is desirable to recover and recycle this precursor.

Figure 9:
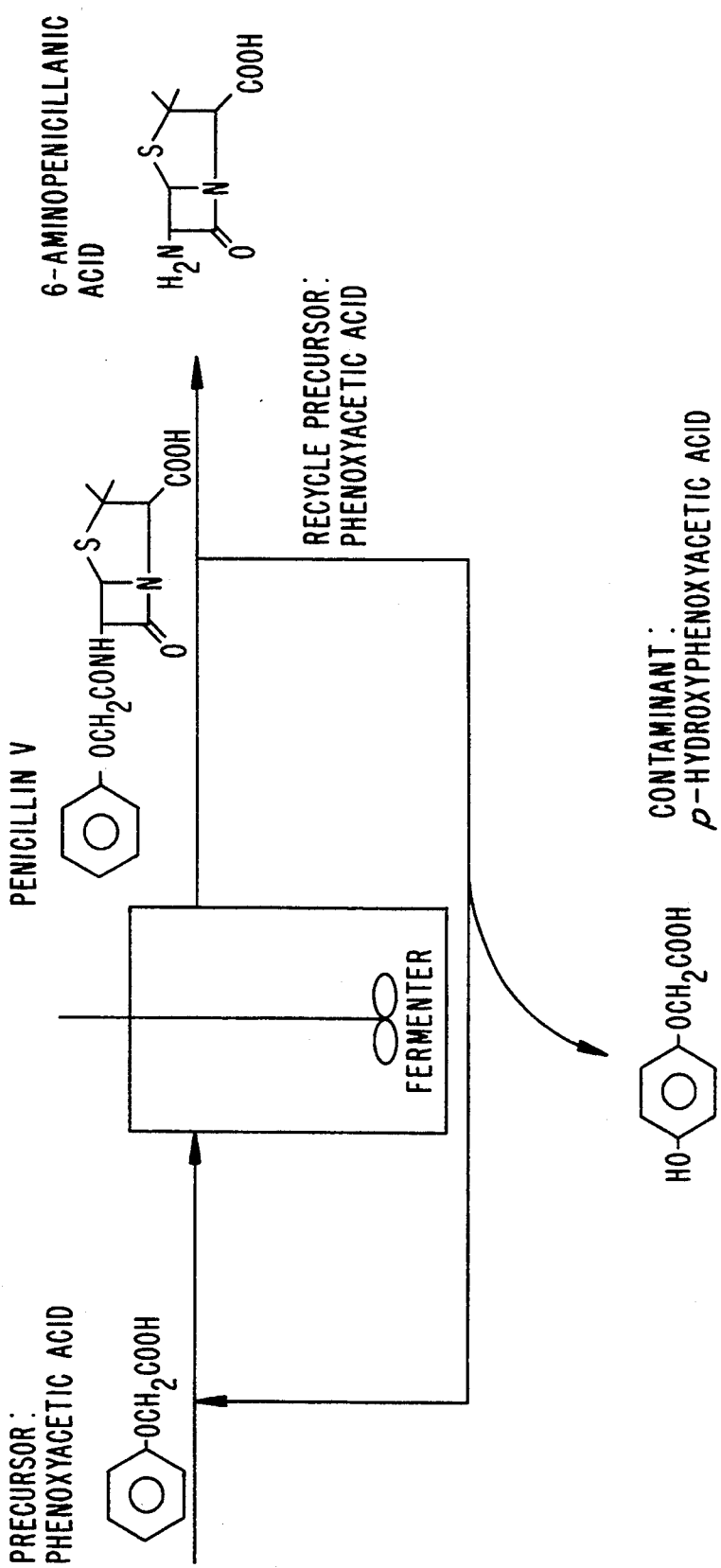
FIG. 9 is a schematic illustrating the recycling of the phenoxyacetic acid precursor and the tyrosinase reaction/chitosan adsorption approach for selectively removing the p-hydroxyphenoxyacetic acid contaminant from the recycle stream. It should be noted that due to the batch nature of typical fermentations, the precursor recovered from one fermentation is likely to be reused in subsequent fermentations.

In general, it is common in recycle operations that undesired chemical contaminants tend to accumulate in recycle streams. For penicillin V manufacturing, the undesired contaminant is p-hydroxyphenoxyacetic acid which results from the hydroxylation of the phenoxyacetic acid precursor by the penicillin-producing culture. This hydroxylated contaminant can be utilized by the cells to produce the hydroxylated penicillin V analogue (Chang et al, 1991 *J. Indus. Microbiol.* 7:175–180; Lein, J., 1986 p. 105–139 In Z. Vanek and Z. Hostalek (eds). Overproduction of Microbial Metabolites. Butterworths). Obviously the formation of this hydroxylated penicillin analogue is undesirable if the penicillin V is to be used directly as a therapeutic. In addition, the formation of the hydroxylated penicillin V represents a yield loss even if the penicillin V is to be used for producing semisynthetic $\beta$-lactams, especially cephalosporins (Chang et al, 1991 *J. Indus. Microbiol.* 7:175–180). To avoid the formation of the hydroxylated penicillin V analogue, genetic strategies have been investigated to eliminate the culture's ability to hydroxylate the phenoxyacetic acid precursor (Chang et al, 1991 *J. Indus. Microbiol.* 7:175–180). Unfortunately these genetic approaches have not been entirely successful in eliminating the formation of the hydroxylated precursor or product. Thus to prevent the recycling of the hydroxyphenoxyacetic acid, it is desirable to simply and selectively remove this contaminant from the recycle stream. FIG. 9 summarizes such a recycle operation wherein contaminated p-hydroxyphenoxyacetic acid is selectively removed from such a recycle stream.

Figure 13:
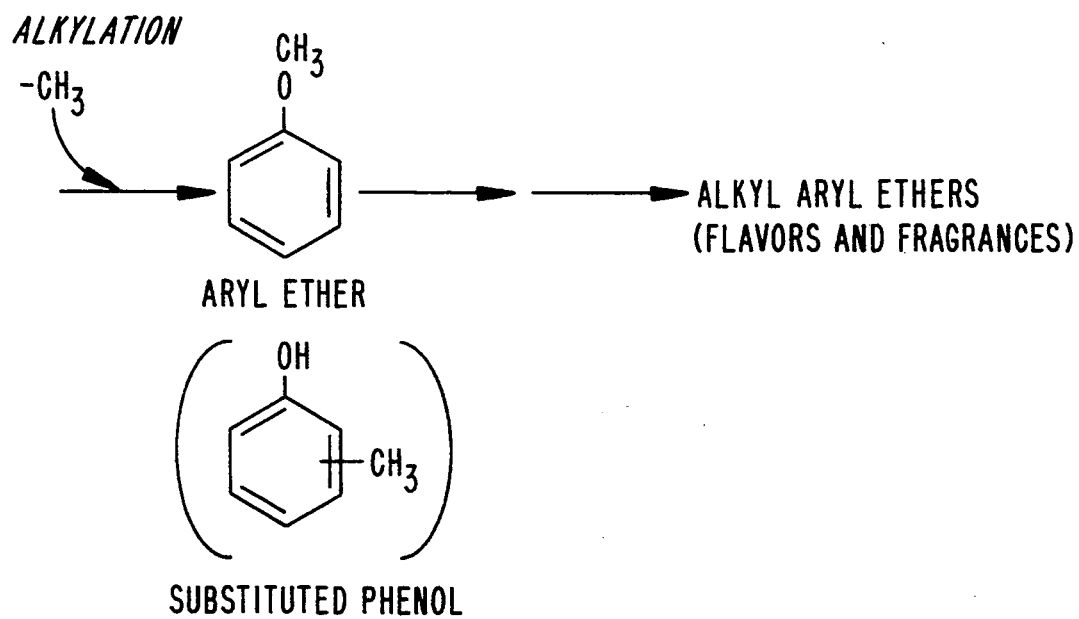
FIG. 13 is a schematic for upgrading an intermediate process stream. Because alkylation catalysts are not entirely selective, alkyl aryl ethers are produced along with substituted phenolic byproducts. To upgrade the intermediate process stream in alkyl aryl ether manufacturing it is necessary. to selectively remove the contaminating phenolic byproduct.

The present invention is also applicable to the synthesizing of aryl ethers. Aryl ethers, which are commonly used for fragrance and flavors, are synthesized in a sequence of reactions. Although the sequence may vary, there is generally an alkylation or allylation as one of the early reaction steps. Using anisole-based ethers (e.g. anisaldehyde, anise alcohol and anethole) as an example, FIG. 13 sketches such a sequence. Despite considerable efforts over the years, entirely selective alkylation catalysts are not yet available and thus alkylation is not confined to the oxygen but some ring alkylation is observed with the formation of a substituted phenolic byproduct. Unless removed, the contaminating phenolic byproduct is likely to react with reagents in subsequent reaction steps and both wastefully consume reagents and result in the generation of more waste. Although alternative phenol removal techniques could be considered for upgrading this intermediate process stream TR/CA is attractive for small volume producers because implementation of TR/CA would require little investment in complex, capital equipment. Due to its high selectivity and efficiency for phenol removal (i.e. large separation factors), TR/CA would not require multiple-staged contacting. In addition, few changes in existing process sequences would be needed for implementation of TR/CA.

The present invention can also be applied to removing storage inhibitors in monomer solutions to be used in polymerization processes. In industrial processes, polymers are produced as a mixture with a distribution of molecular weights. Because the final properties of a polymer (e.g. mechanical strength) are significantly dependent on the molecular weight of the polymer, it is necessary to develop production strategies, or separation techniques which yield polymers with a narrow distribution of molecular weights around some optimum. From a waste minimization standpoint, it would be advantageous to develop production strategies which prevent the formation of inappropriately sized polymers rather than separating and disposing of polymers with improper molecular weights. For common free-radical catalyzed vinyl polymerizations (e.g. for polyethylenes, polystyrenes and polyacrylates), it has been particularly difficult to develop production strategies which successfully control the molecular weight distribution. The current limitation to controlling the molecular weight distribution of such polymers is the use of reaction inhibitors in the storage of monomers. Storage inhibitors are required because the high reaction and heat evolution rates of free-radical catalyzed polymerizations can result in serious accidents if such polymerizations are inadvertently initiated during monomer manufacture, storage or transportation. Since it is generally believed that residual storage inhibitors are the cause of variabilities in subsequent polymerization reactions, there is considerable interest in removing these inhibitors using distillation, many companies believe the safety risks of such an operation are unacceptable. Another option is to utilize a caustic aqueous solution to extract the storage inhibitors. This latter option is particularly attractive for suspension and emulsion polymerizations because the organic monomeric phase is added to a continuous aqueous phase for such polymerizations. Unfortunately, the partitioning of the inhibitor into the continuous aqueous phase is incomplete and storage inhibitors have also been observed to bind to and reduce the quality of the final polymeric product. Thus TR/CA represents a desirable alternative for the removal of these compounds.

Another embodiment of the invention focuses on producing chitosanbased biodegradable polymers. Because of its linear structure, the properties of chitosan polymers can be significantly improved by crosslinking. Since it is likely that quinones will crosslink chitosan, a highly specific crosslinking agent, may aid in the development of chitosan-based polymers. It is also possible that tyrosinase could be used to create a unique class of chitosan-lignin co-polymers.

Another embodiment of the present invention includes the use of selfassembly to obtain materials with organized molecular films. In most cases, organics are bound to metal surfaces to produce monolayer films with controlled surface properties. Chitosan can serve as a base for the "selfassembly" of phenols or quinones of varying chemical structures to yield chitosan-based polymers with "engineered" surface properties.

A still further embodiment of the present invention is the development of chitosan-based adsorbents which exploit principles of molecular recognition. As a linear polymer with a large number of ionizable (i.e. amine) and hydrogen bonding (i.e. hydroxyl groups) sites, if chitosan is crosslinked in the presence of a "print" molecule, then a chitosan-based adsorbent could be formed in which a highly selective binding site is "imprinted" or "ternplated" into the crosslinked polymer. In contrast to the use of proteins in which the pre-formed binding site is lost in the presence of water, the binding site in chitosan would be locked in place by crosslinking. Further, if stereo-pure phenolics (e.g. tyrosine) are bound to chitosan, functionalized chitosan supports may be generated which can be used for chiral separations.

Yet another embodiment of the present invention is to provide a method for altering the affinity of a pharmaceutical such that the pharmaceutical more specifically and/or efficiently binds a desired target compound or molecule.

In order that those skilled in the art can more fully understand the present invention and advantages thereof, the following examples are set forth. These examples are given solely for the purpose of illustration, and should not be considered as expressing limitations unless so set forth in the appended claims.

EXAMPLES

Mushroom tyrosinase (EC 1.14.18.1) of specific activity 1050 units/rag (activity determined by supplier) was purchased from Worthington Biochemicals (Freehold, NJ). Chitosan from crabshells and activated charcoal were used as adsorbing surfaces and were purchased from Sigma Chemical Co. (St. Louis, MO). In addition to phenol, p-cresol and pyrocatechol (1,2-benzenediol) were also studied. These phenols and all other chemicals used in this study were obtained commercially and were of analytical grade.

In studies involving an enzymatic reaction, mushroom tyrosinase was added to 50 mM phosphate buffer (pH 6.8) containing a single phenolic. In studies involving both an enzymatic reaction and chitosan adsorption, mushroom tyrosinase and chitosan were added simultaneously to a 50 mM phosphate buffer (pH 6.8) containing a single phenolic. Reactions were conducted at 25° or 27° C. in bottles containing small volumes of liquid (either 10 or 25 ml), which were agitated either by shaking or by using a stir bar. The reaction kinetics were measured by monitoring changes in dissolved oxygen (DO) using a dissolved oxygen meter (Microelectrodes, Londonderry, NH).

Adsorption heat (Q) was measured using an adiabatic solution calorimeter (Parr Instrument Company, Moline, IL). The temperature difference, $\Delta T_c$, between the baselines of a typical thermogram as shown in FIG. 1, is used to calculate the adsorption heat using the equation $$Q = S(\Delta T_c - \Delta T_0) \quad (6)$$

where $\Delta T_o$ accounts for the heat of wetting and is the temperature rise observed in a control where sorbent was contacted with distilled water containing no solute. S is the heat capacity of the system and is given by $$S = C_{pi}m_i = C_{ps}m_s S_c \quad (7)$$

$C_{pi}$ is the heat capacity of the solution (1.0 cal/g.° C.), $m_i$ is the mass of the solution (100 g), $S_c$ is the heat capacity of the calorimeter (21.4 cal/° C.), $C_{ps}$ is the specific heat capacity of the sorbent, and ms is the mass of sorbent. Although an accurate measure of $C_{ps}$ is unavailable, the second term on the right hand side of equation 7 is typically small (Maity et al., 1991).

Adsorption enthalpy ($\Delta H°$) was determined from the slope of the adsorption heat versus amount of solute adsorbed. It should be noted that calorimetric studies were done in distilled water (and not buffered solutions) to avoid the large temperature rise observed when chitosan was contacted with the phosphate buffer.

Liquid-phase quinone and phenolic concentrations were measured or estimated using ultraviolet spectrophotometry (Gilford Response, Oberlin, OH). When liquid-phase concentrations were measured, the wavelength of maximum absorption was used. For adsorption studies, the amount of solute adsorbed was calculated from the difference between the initial (prior to sorbent addition) and final (after equilibration) solute concentrations (C° and C, respectively) using the equation $$\text{amount adsorbed} = (C° - C)V_L \quad (8)$$

where $V_L$ is the solution volume.

Example 1

Quinone-Chitosan Adsorption

To characterize chitosan adsorption, calorimetric studies were performed in which chitosan was contacted with aqueous solutions containing quinone. Because the o-quinone which is generated from the tyrosinase reaction is unstable and not readily available, p-quinone was used for adsorption studies.

Chitosan (12 g) was added to an aqueous solution (100 g) containing 5 mM p-quinone. As shown in FIG. 1, the temperature in the calorimeter increased above the initial, preadsorption baseline. Approximately 1 rain after chitosan addition, the temperature rise slowed and a second baseline was observed.

The $\Delta T_c$ was observed to be 0.036° C., which when converted into an adsorption heat by equation 6, compared to 0.0085° C. observed when chitosan was added to distilled water without p-quinone.

Figure 2:
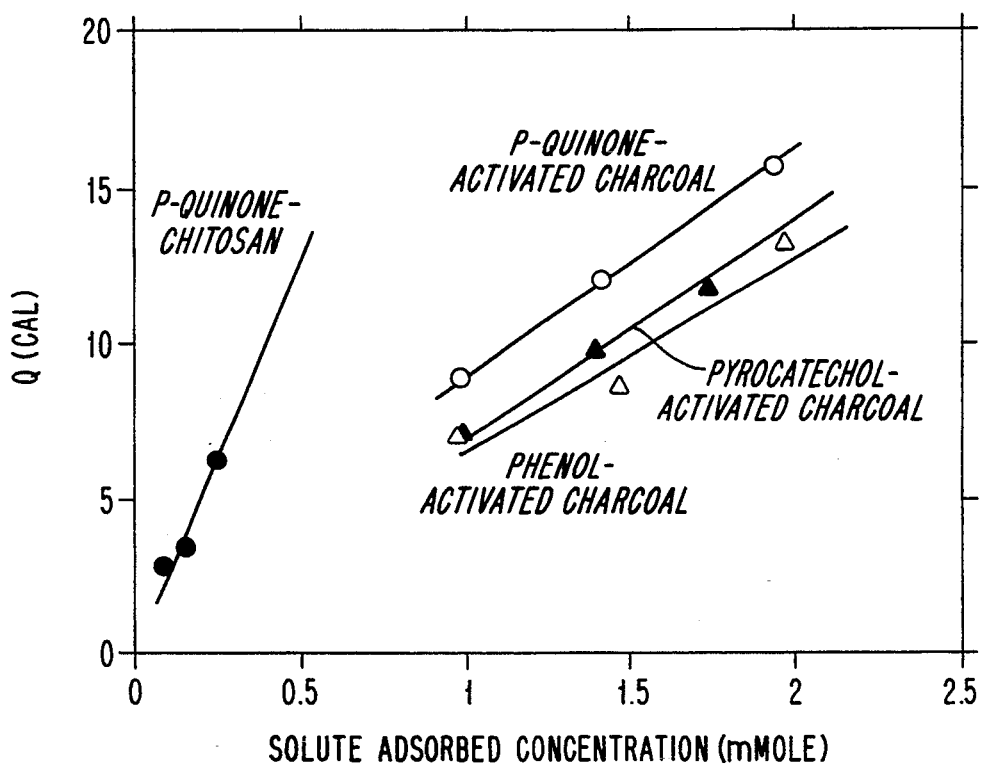
FIG. 2 is a graph showing heat versus amount of solute adsorbed for adsorption onto chitosan and activated charcoal.

The aqueous-phase quinone concentration, both before and after adsorption, was also measured to determine the amount of quinone adsorbed (i.e., by equation 8). As shown in FIG. 2, when initial quinone concentrations were varied, the adsorption heat increased linearly with the amount of quinone adsorbed. From the slope of FIG. 2, the adsorption enthalpy for quinone and adsorption onto chitosan was calculated to be −24.7 kcal/mol.

TABLE I

Adsorption Enthalpies of Phenol, Pyrocatechol, and p-Quinone with Activated Charcoal and of p-Quinone with Chitosan

| solute | Adsorption enthalpy ($\Delta H°$), kcal/mol | |
|---|---|---|
| | activated charcoal | chitosan |
| phenol | −6.4 | |
| pyrocatechol | −6.7 | |
| p-quinone | −7.3 | −24.7 |

Adsorption enthalpies of this magnitude are generally believed to result from strong, presumably covalent interactions and such adsorption is referred to as chemisorption. Thus, the results in FIGS. 1 and 2 demonstrate that quinone adsorption onto chitosan was rapid (on the order of only minutes) and strong.

For comparison purposes, the adsorption of phenols and quinones onto activated charcoal was examined. As shown in FIG. 2 and Table I, considerably less heat was evolved for adsorption onto activated charcoal. The observed enthalpies for phenols and p-quinone adsorption onto activated charcoal were between to be −6 and −7 kcal/mol, suggesting that adsorption onto activated charcoal involved low-energy physical forces (e.g., hydrophobic interactions).

This illustrates that the strong binding of the quinone to chitosan confers high efficiency for the removal of low concentrations of quinone.

It should be noted that since the phenols are not adsorbed onto chitosan, adsorption enthalpies for these solutes onto chitosan are not reported in Table I.

Example 2

Effect of Chitosan on Tyrosinase Activities. Stoichiometry.

To examine the stoichiometry of the tyrosinase reactions, a dissolved oxygen probe was used to measure oxygen consumption under experimental conditions which established low initial phenol concentrations. Reactions with differing initial cresol concentrations were conducted in buffered solutions (50 mM phosphate) at a pH of 6.8 with 32 units/ml tyrosinase. Chitosan was not added in this experiment.

Figure 3:
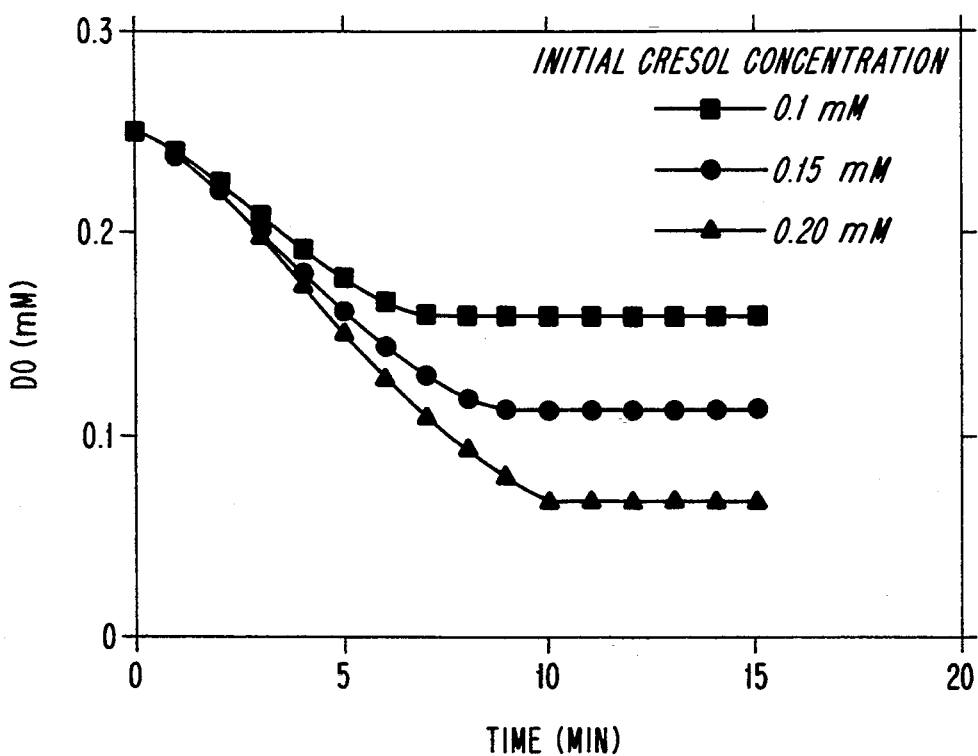
FIG. 3 is a graph showing dissolved oxygen versus reaction time for the tyrosinase-catalyed oxidation of cresol.

As shown in FIG. 3, the dissolved oxygen decreased over time until a constant value was reached. Presumably, the tyrosinase reaction ceased after longer reaction times due to the depletion of the phenol reactant. When higher initial phenol concentrations were used, FIG. 3 shows that the final dissolved oxygen concentration was lower.

Figure 4A:
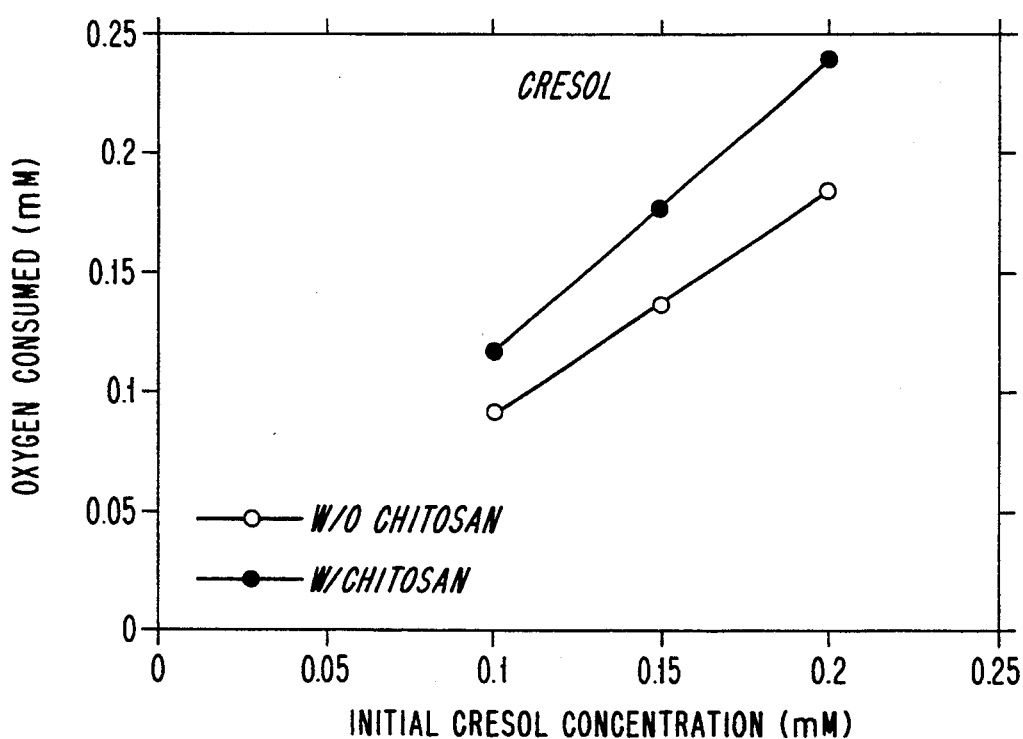
FIGS. 4A and 4B are a pair of graphs showing total oxygen consumption versus initial substrate concentration for the tyrosinase-catalyzed reaction with A) the monophenol cresol, or B) the o-diphenol pyrocatecol, in the presence (w/) and absence (w/o) of chitosan.
Figure 4B:
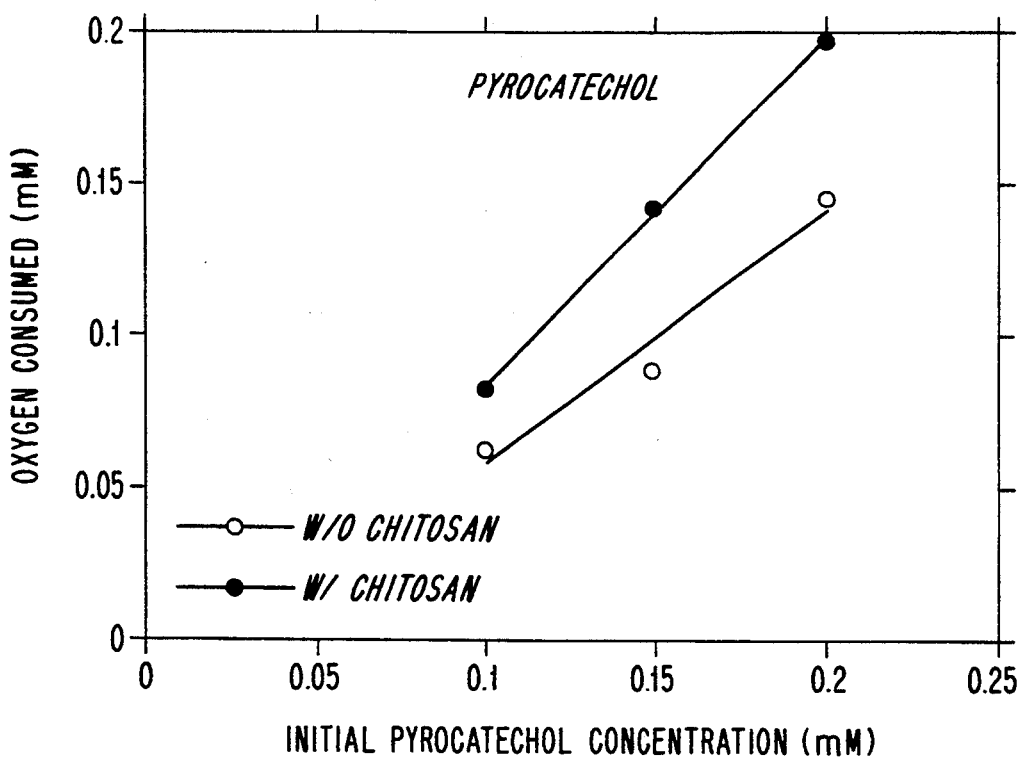

Plots of the total oxygen consumed versus the initial phenol concentration are shown in FIG. 4. The fact that these plots are linear supports the contention that the phenols were the limiting reactants in these studies. Thus, the slopes of FIG. 4 were used to determine the stoichiometric coefficients between oxygen and phenol consumption.

For the stoichiometric coefficients listed in Table II, three observations can be made.

TABLE II

Stoichiometric Ratio of Oxygen Consumption per Mole of Phenol Oxidized in the Presence and Absence of Chitosan

| | stoichiometric coefficients, mol of $O_2$/mol of phenol | | ratio of stoichiometric coefficients with and |
|---|---|---|---|
| phenol | w/o chitosan | w/chitosan | without chitosan |
| p-cresol | 0.94 | 1.24 | 1.32 |
| pyrocatechol | 0.84 | 1.15 | 1.37 |

First, the ratio of oxygen consumed per initial phenol is greater for the monophenol cresol than for the diphenol pyrocatechol. Qualitatively, this difference is expected since monophenols are expected to undergo two oxidation reactions (oxidation of a monophenol to a diphenol and oxidation of the phenol to a quinone), while o-diphenols can only undergo the single oxidative reaction (oxidation to a quinone). Secondly, the stoichiometric coefficients observed in Table II cannot be quantitatively predicted from expected reaction stoichiometries in which quinones are the ultimate product. Differences between expected and observed oxygen stoichiometries for tyrosinase-catalyzed reactions are not uncommon and oxygen to phenol ratios similar to those shown in Table II have been observed in other studies (Wright and Mason, *J. Biol. Chem.*, 1946, vol. 165, pp. 45-53; Mason and Wright, *J. Biol. Chem.*. 1949 vol. 180, pp. 235-247; Horowitz and Shen, *J. Biol. Chem.*, 1952, vol. 197, pp. 513-520; Dawson and Tarpley, *An. N.Y. Acad. Sci.*, 1963, vol. 100, pp. 937-950; Mayer et al., *Phytochemistry*, 1966, vol. 5, pp. 783-789).

However, in the other studies mentioned in the previous paragraph, oxygen to phenol ratios were observed to vary with reaction conditions, initial phenol concentration, and the actual products formed from the reaction. It is possible that variation in this stoichiometric coefficient results from differences in the types and degrees of oxidation of the polyphenolic species formed from the reactions.

Finally, it is noted that in Table II more oxygen was consumed per phenol when chitosan was present. Although the reason for this increased oxygen consumption in the presence of chitosan is unknown, it is possible that more oxidized species are adsorbed by chitosan. This possibility is supported by a couple of additional observations. When p-quinone was adsorbed onto chitosan in the absence of tyrosinase, no oxygen consumption was observed. Also, if tyrosinase was added after p-quinone was adsorbed to chitosan, no oxygen consumption was observed. Thus, it seems unlikely that the increased oxygen consumption in the presence of chitosan could be explained by an oxygen requirement either during or after adsorption.

Example 3

Kinetics: High Enzyme Activities

Figure 5:
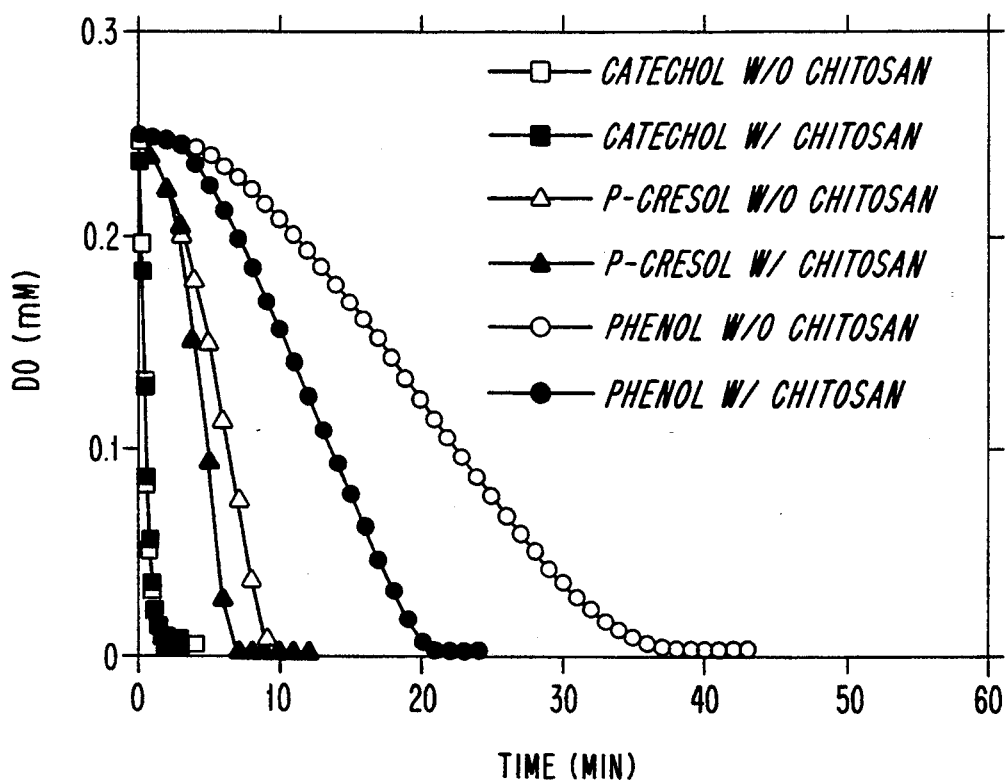
FIG. 5 is a graph showing dissolved oxygen versus reaction time for the tyrosinase-catalyzed oxidation of pyrocatecol, phenol, and cresol in the presence (w/) any absence (w/o) of chitosan.

FIG. 5 shows oxygen consumption when relatively high levels of tyrosinase (55 units/mL) and phenols (0.5 mM) were used. When the phenolic substrate was the o-diphenol pyrocatechol, FIG. 5 shows the dissolved oxygen decreased rapidly. For the monophenols phenol and cresol, a more complex kinetic pattern was observed. For these monophenols, a low initial rate was followed by a somewhat greater rate. This low initial rate is often termed a "lag". (Vaughan and Butt, *Biochem. J.*, 1970, vol. 119, pp. 89-94; Duckworth and Coleman, *J. Biol. Chem.*, 1970;, vol. 425 (7) pp. 1613–1625; Lerch and Ettlinger, *Eur. J. Biochem.* 1972, vol. 31, pp. 427–437; Mcintyre and Vaughan, *Biochem. J.*, 1975, vol. 149, pp. 447–461). After the lag, FIG. 5 shows that the rate of reaction for the monophenols always remains considerably less than that for the o-diphenol.

In the presence of chitosan it can be seen that the rate of oxygen consumption for the o-diphenol pyrocatechol was not significantly altered. In contrast, the rate of oxygen consumption for the reaction of the monophenols phenol and cresol was enhanced in the presence of chitosan. To quantify this enhancement, the oxygen consumption rate for cresol was estimated over the region where the dissolved oxygen decreased nearly linearly over time (i.e., the reaction rates were nearly constant between 0.2 and 0.04 mM dissolved oxygen). This estimate as well as those obtained when a somewhat lower enzyme level were used are reported in Table III. It can be seen that the ratio of the oxygen consumption rates in the presence and absence of chitosan varies between 1.3 and 1.5. This ratio is similar to the ratio of the oxygen stoichiometries in the presence and absence of chitosan, which was observed to be 1.3 (Table II). Thus, despite an increase in the rate of oxygen consumption, if differences in oxygen stoichiometries are accounted for, it appears that the reaction of cresol may actually not be enhanced in the presence of chitosan. At worst, the results in FIG. 5 and Table III demonstrate that chitosan does not inhibit tyrosinase activities.

TABLE III

Oxygen Consumption Rates for Tyrosinase-Catalyzed Oxidation of p-Cresol and Ratio of These Rates in the Presence and Absence of Chitosan When Different Levels of Tyrosinase Were Used

| tyrosinase activities | rate of oxygen consumption, mmol/L-h | | ratio of oxygen consumption rates with and without chitosan |
|---|---|---|---|
| | w/o chitosan | w/chitosan | |
| 14 units/mL | 0.82 | 1.11 | 1.35 |
| 55 units/mL | 2.04 | 3.11 | 1.52 |

Kinetics: Low Enzyme Activities

Figure 6:
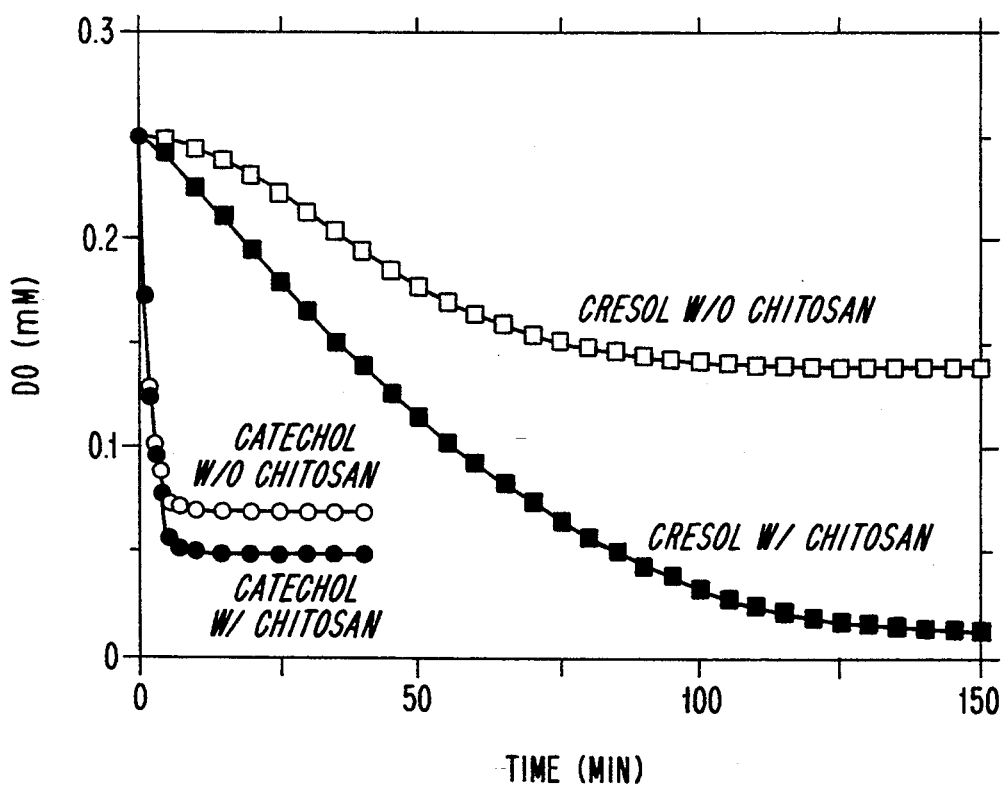
FIG. 6 is a graph showing dissolved oxygen versus reaction time for the tyrosinase-catalyzed oxidation of pyrocatecol and cresol in the presence (w/) and absence (w/o) of chitosan.

To further explore the effect of chitosan on tyrosinase performance, the reaction was examined when relatively low levels of tyrosinase (1.4 units/mL) and high levels of phenols (0.5 mM) were used. Under these conditions, the suicide inactivation of tyrosinase is expected to be most evident. Suicide inactivation appears to result because the quinones formed from the tyrosinase-catalyzed reaction are capable of reacting with and inactivating the tyrosinase enzyme. For the case of the o-diphenol pyrocatechol, FIG. 6 shows that, in the presence of chitosan, the total amount of oxygen consumed increased (0.20 versus 0.18 mM oxygen consumed). However, because of differences in the oxygen stoichiometries (Table II), it is possible that the actual oxidation of pyrocatechol was not enhanced in the presence of chitosan. Thus chitosan does not appear to limit tyrosinase inactivation for the case of this o-diphenol.

The reaction of the monophenol cresol was also examined. In the absence of chitosan, FIG. 6 shows that, after a lag, a period of rapid reaction slowed and ultimately stopped. Again, it is believed that the cessation in reaction resulted from the inactivation of tyrosinase. In the presence of chitosan, the reaction with cresol was observed to proceed faster and over a longer period.

Even when differences in the stoichiometries of oxygen consumption are accounted for, considerably more reaction occurred in the presence of chitosan. Thus, it appears that, for the monophenolic substrate, chitosan was able to reduce tyrosinase inactivation.

Qualitative Kinetic Model

One possible interpretation of the above results utilizes the following qualitative reaction scheme:

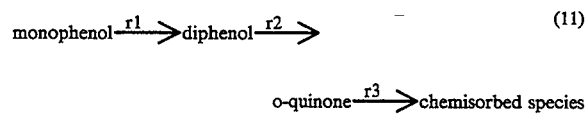

$$\text{monophenol} \xrightarrow{r_1} \text{diphenol} \xrightarrow{r_2} \quad (11)$$

$$\text{o-quinone} \xrightarrow{r_3} \text{chemisorbed species}$$

where the monophenol is converted to the o-diphenol at rate $r_1$, the o-diphenol is convened to the o-quinone at $r_2$, and the o-quinone is chemisorbed at $r_3$. Under the conditions studied here, FIGS. 5 and 6 show that the second reaction occurs over the course of seconds to a few minutes, while the first reaction occurs over the course of several minutes to hours. The calorimetric study (FIG. 1) suggests that chemisorption may occur at a rate intermediate between the two enzymatic reactions. From this analysis, it appears that $$r_2 > r_3 > r_1 \quad (12)$$

The relative rates proposed above are reasonably supported from oxygen consumption measurements in the presence and absence of chitosan (FIGS. 5 and 6). If, as proposed above, $r_2 > r_3$, then the reaction of the o-diphenol would result in a significant transient accumulation of the intermediate o-quinone. In the extreme of $r_2 > r_3$, the initial oxygen consumption rate for the reaction of the o-diphenol should reflect only the second reaction and be independent of the presence or absence of chitosan. FIGS. 5 and 6 show that, for pyrocatechol oxidation, the initial oxygen consumption rate in the presence and absence of chitosan is similar. Small differences in oxygen consumption rates and differences in the oxygen consumption stoichiometries in the presence and absence of chitosan (Table II) could result in differences in the final amount of oxygen consumed for pyrocatechol oxidation. Such differences were observed in FIG. 6.

If $r_1$ is much less than either $r_2$ or $r_3$, then the first oxidation step would be rate limiting such that the monophenols would be chemisorbed as soon as they were oxidized. In this case, the initial oxygen consumption rates for monophenol oxidation should reflect all the reactions. Thus, the initial rate of oxygen consumption for reaction of the monophenols should vary in the presence and absence of chitosan due to differences in the oxygen consumption stoichiometries (Table II). This difference in initial oxygen consumption rate was observed in FIGS. 5 and 6.

Since the proposed reaction scheme and relative rates are qualitatively capable of explaining the various observations, this qualitative model was used to suggest a reason why chitosan can stabilize tyrosinase for monophenolic but not for diphenolic substrates. For the monophenolic substrates, the above model suggests that since the first reaction is slow, then low levels of intermediate quinones will accumulate in the presence of chitosan. Since quinones have been reported to cross-link proteins (Leatham et al., *Phytopathology*, 70:1134–40, 1980) it is possible that these intermediates are a significant cause of suicide inactivation of tyrosinase. Thus it is possible that chitosan stabilizes tyrosinase by limiting the accumulation of quinones. In contrast, since $r_2$ is proposed to be greater than $r_3$, when diphenolic substrates are used, quinones will be produced faster than they can be adsorbed. Again, if quinones are a major cause of tyrosinase inactivation, then the inability of chitosan to prevent quinone accumulation with the diphenolic substrates may explain chitosan's inability to stabilize the enzyme with pyrocatechol.

In summary, results from kinetic studies can be qualitatively explained by the reaction scheme and relative rates proposed above and by the assumption that the accumulation of intermediate quinones accelerates tyrosinase inactivation. This qualitative model provides a simple means to explain the kinetic data for this complex, if not intractable, reaction system.

Repeated Use of Tyrosinase for Cresol Oxidation

Figure 7A:
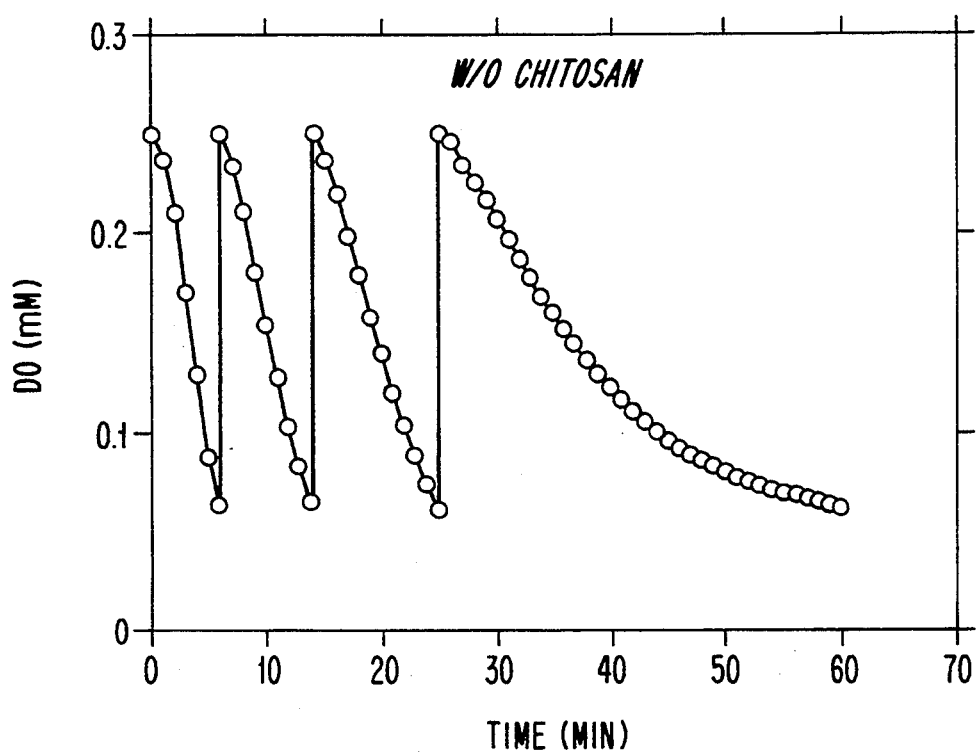
FIGS. 7A and 7B are a pair of graphs showing dissolved oxygen versus reaction time for the repeated reaction of cresol with tyrosinase, in A) in the absence (w/o) of chitosan, and B) in the presence (w/) of chitosan [5 % (w/v)].
Figure 7B:
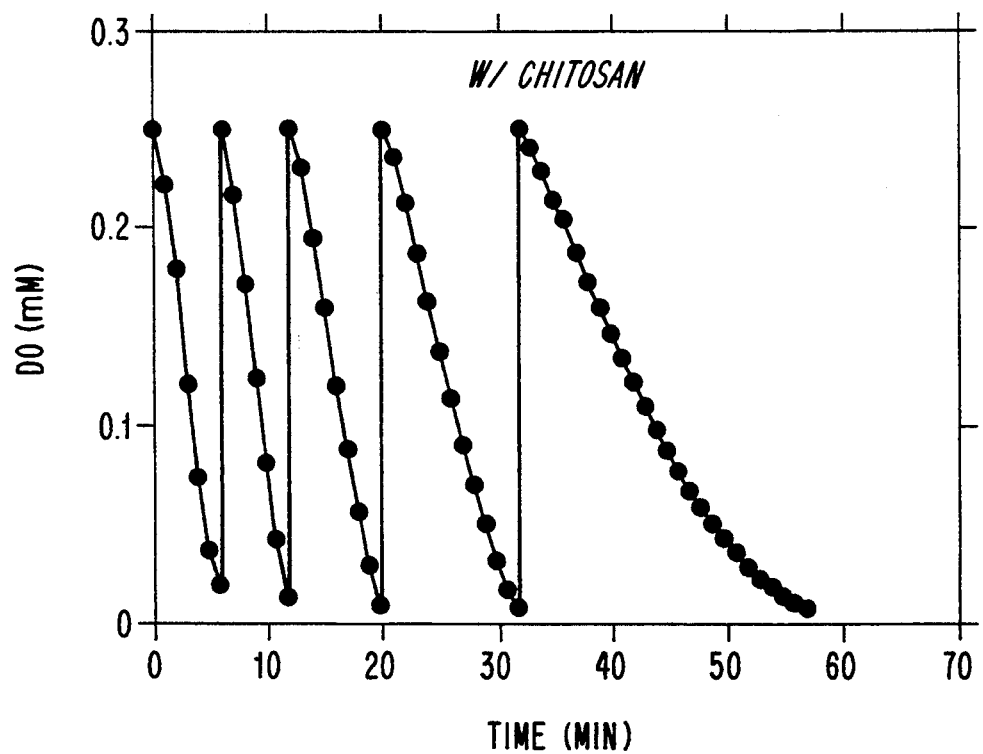

To further examine the ability of chitosan to stabilize tyrosinase for monophenolic substrates, a long-term study was conducted with high initial tyrosinase activities (55 units/mL) and repeated cresol additions. FIG. 7A shows results when 0.2 mM cresol was initially added to an oxygen-saturated solution containing tyrosinase. After addition of cresol, the dissolved oxygen decreased rapidly until approximately 0.06 mM oxygen remained. From stoichiometric considerations (Table II), this level of oxygen consumption corresponds to the complete conversion of cresol. When the dissolved oxygen reached 0.06 mM, air was bubbled through the solution for half an hour to obtain oxygen saturation. After air was bubbled through, 0.2 mM cresol was added, and the reaction was allowed to continue for a second cycle. As shown in FIG. 7A, the reaction rate decreased with each subsequent reaction cycle until the reaction essentially ceased during the fourth cycle. FIG. 7B shows results from a similar experiment where chitosan was added to the reaction cycle. Because of differences in oxygen stoichiometries, the dissolved oxygen was allowed to decrease from saturation (0.24 mM) to 0.01 mM to permit complete conversion of cresol in the presence of chitosan. As seen in FIG. 7B, the tyrosinasecatalyzed reaction rate was not reduced until the third cycle and the reaction continued through the fifth cycle. For comparison, Table IV lists the reaction rates estimated from the individual cycles for reactions in the presence and absence of chitosan. Again chitosan enhanced the reaction with cresol, due presumably to the stabilization of tyrosinase by removal of the reactive quinones.

TABLE IV

Oxygen Consumption Rates for Tyrosinase-Catalyzed Oxidation of p-Cresol for Repeated Reactions in the Presence and Absence of Chitosan

| reaction cycles | rate of oxygen consumption, mmol/L-h | |
|---|---|---|
| | w/o chitosan | w/chitosan |
| first cycle | 1.92 | 2.52 |
| second cycle | 1.38 | 2.46 |
| third cycle | 1.02 | 1.92 |
| fourth cycle | 0.49 | 1.32 |
| fifth cycle | | 0.72 |

Tyrosinase Reaction/Chitosan Adsorption

Figure 8A:
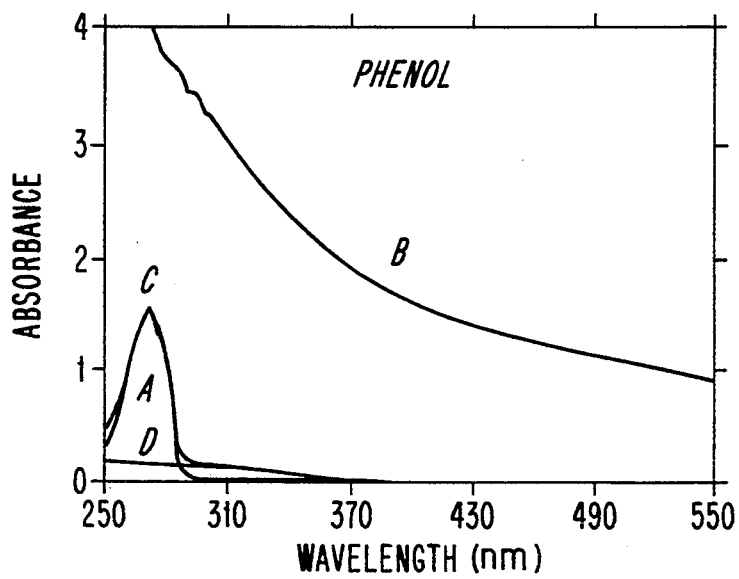
FIGS. 8A, 8B, and 8C are graphs showing enzymatic reaction/adsorption of (A) phenol, (B) cresol, and (C) pyrocatecol. Curve A: Phenolic added alone. Curve B: Phenolic plus mushroom tyrosinase added. Curve C: Phenolic plus chitosan. Curve D: Phenolic plus mushroom tyrosinase plus chitosan.
Figure 8B:
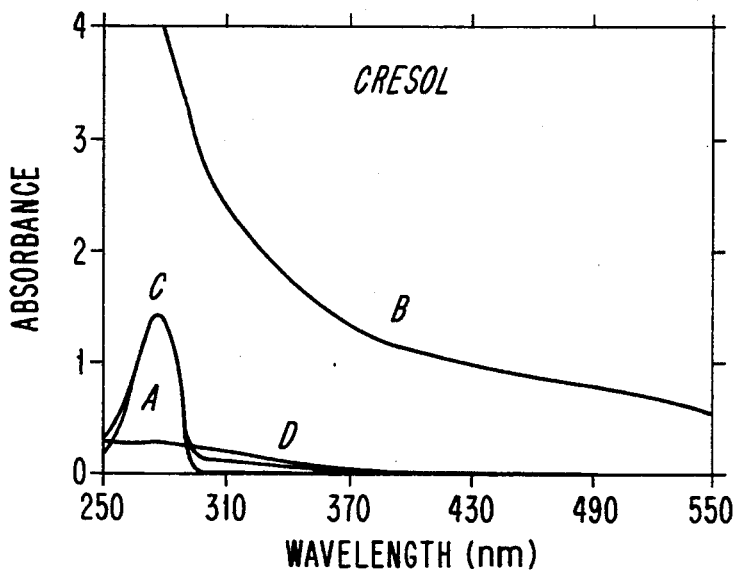
Figure 8C:
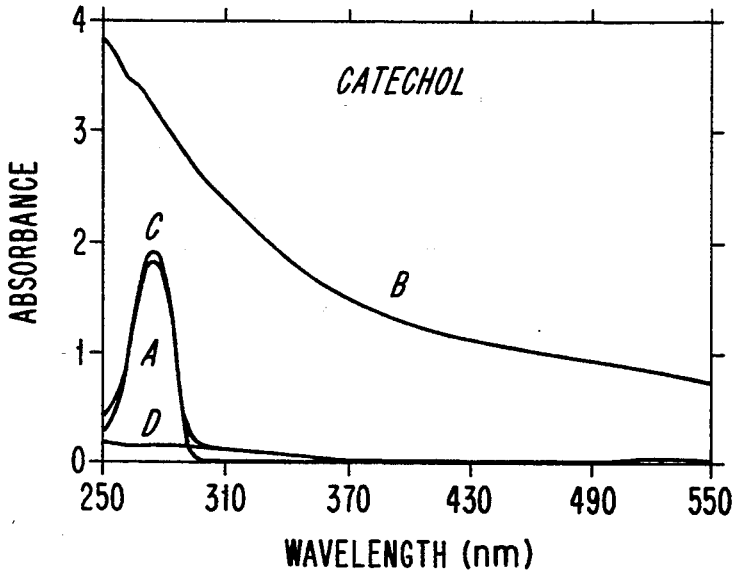

From the previous results, it can be seen that p-quinone is strongly bound to chitosan, that chitosan does not adversely affect the activities of tyrosinase, and that for monophenolic reactants chitosan may even stabilize tyrosinase. To demonstrate that the twostep, tyrosinase reaction/chitosan adsorption operation was capable of removing phenols from solution, solutions containing either a monophenol (phenol or cresol) or the o-diphenol pyrocatechol were examined. Curves A of FIG. 8 show the ultraviolet (UV) absorbance of the controls in which neither tyrosinase nor chitosan was added. When mushroom tyrosinase was added to the phenol solutions, there was a shift in the maximum UV absorbance from 270 nm (characteristic of phenols) to approximately 380–400 nm characteristic of the quinones (Duckworth and Coleman, J. Biol. Chem. 245:1613–1625, 1970). Over the 2-h period of this experiment, the quinone peak decreases (not shown), presumably due to oligomerization reactions and polyphenol formation. The UV absorbances of the phenol solutions after incubation for 2 h with tyrosinase are shown in curves B. If, instead of enzyme, chitosan was contacted with the phenolic solutions (curves C), there was no shift but rather a small increase in the UV absorbance as compared to the controls (i.e., curves A). Thus chitosan was unable to catalyze the conversion of the phenols (as expected), and also, chitosan was unable to adsorb the phenols from these dilute solutions. When the phenol solutions were simultaneously contacted with mushroom tyrosinase and chitosan (curves D), it can be seen that there was nearly a complete reduction in UV absorbances. Thus these results show that the combination of tyrosinase reaction and chitosan adsorption was capable of removing UV-absorbing material (i.e., phenols and quinones) from dilute solutions.

Example 4

Removal of p-hydroxyphenoxyacetic acid from a Fermentation Recycle Stream

Mushroom tyrosinase (EC 1.14.18.1) was purchased from Worthington Biochemicals (Freehold, NJ). Chitosan from crab shells was purchased from Sigma Chemicals (St. Louis, MO). Phenoxyacetic and p-hydroxyphenoxyacetic acids were purchased from Pflatz and Bauer (Waterbury, CT). A schematic of the recycling of the phenoxyacetic acid precursor is illustrated in FIG. 9.

All experiments were conducted in a 50 mM phosphate buffer (pH 6.8). When added, mushroom tyrosinase was added to a final activity of 50 Units/mL (activity was determined by the supplier) while chitosan was added to 5 w/v %. All reactions were conducted in 10 mL (liquid volume) bottles which were shaken and incubated at room temperature for 1 hour.

To monitor the progress of the enzyme-catalyzed reaction, a dissolved oxygen electrode was used (Microelectrodes, Londonderry, NH) (Mayer et al, (1966), Phytochem. 5:783–789). To examine the enzymatic reaction and adsorption in terms of the aqueous-phase phenoxyacetic and hydroxyphenoyacetic acids, UV-visible spectrophotometry was used. When chitosan was added to the reaction, the solid flakes were filtered away prior to UV analysis of the solution.

Figure 10:
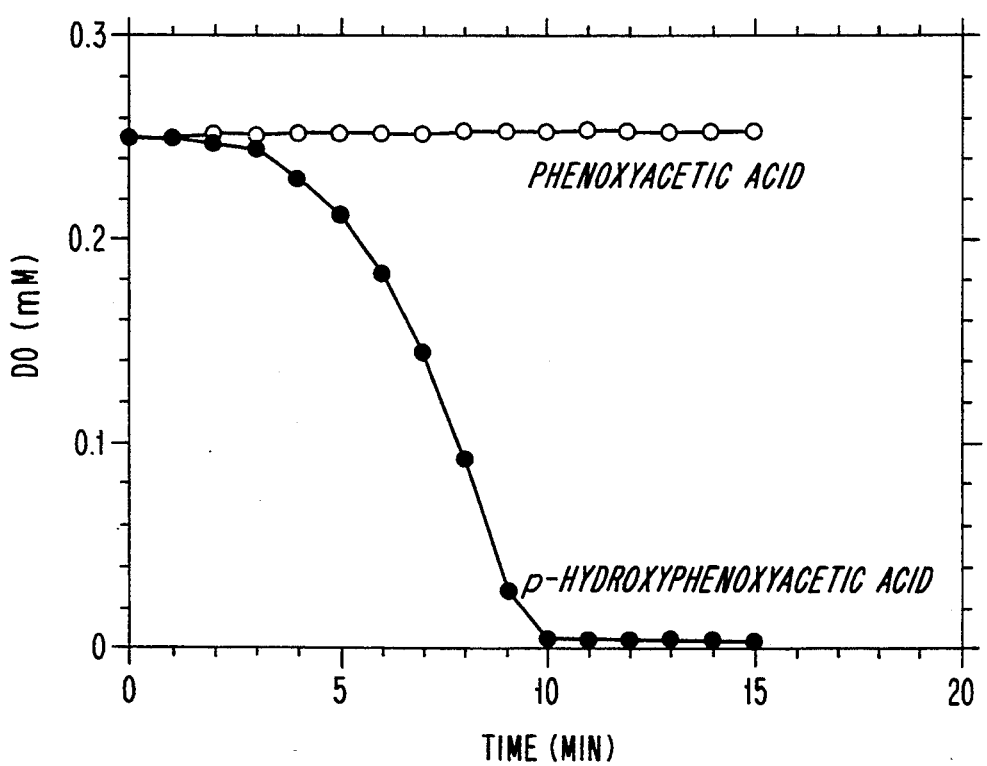
FIG. 10. Selectivity of the tyrosinase-catalyzed reaction. Mushroom tyrosinase (200 Units/ml) was added to 50 mM phosphate (pH 6.8) solutions containing 0.5 mM of either phenoxyacetic or p-hydroxyphenoxyacetic acid. The tyrosinase-catalyzed reaction was monitored by following the loss of the oxygen reactant.

To examine the selectivity of the enzymatic reaction, tyrosinase was added to solutions containing either phenoxyacetic acid or phydroxyphenoxyacetic acid. The tyrosinase catalyzed reaction was examined by monitoring changes in the oxygen reactant using a dissolved oxygen probe. The results in FIG. 10 show that the dissolved oxygen level decreased when tyrosinase was added to the solution containing p-hydroxyphenoxyacetic acid while no reaction was observed when tyrosinase was added to the solution containing phenoxyacetic acid. Thus tyrosinase appears to specifically react with the hydroxylated contaminant.

Figure 11A:
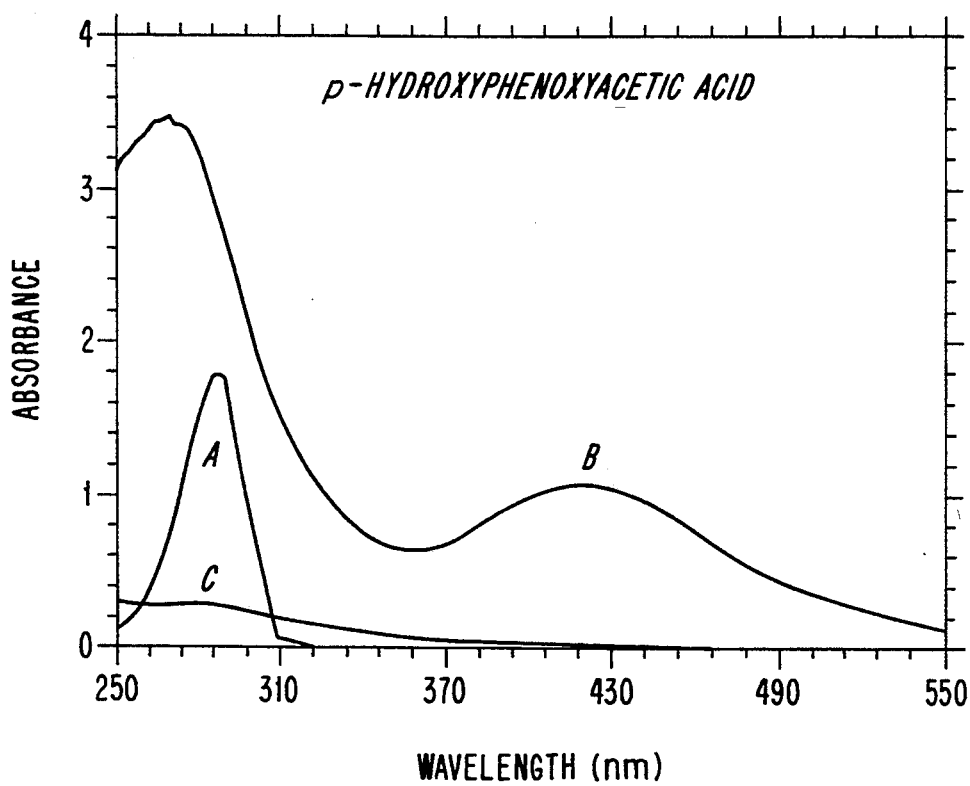
FIG. 11. Selectivity of chitosan adsorption for the tyrosinase-catalyzed reaction products. (A) The UV absorbance of solutions containing: 0.7 mM p-hydroxyphenoxyacetic acid (Curve A); 0.7 mM p-hydroxyphenoxyacetic acid and 50 Units/mL mushroom tyrosinase (Curve B): 0.7 mM p-hydroxyphenoxyacetic acid and 50 Units/mL mushroom tyrosinase and 5 w/v chitosan (Curve C). (B) The UV absorbance of solutions containing: 1 mM phenoxyacetic acid (Curve A); 1 mM phenoxyacetic acid and 50 Units/mL mushroom tyrosinase (Curve B); 1 mM phenoxyacetic acid, 50 Units/mL mushroom tyrosinase and 5 w/v % chitosan (Curve C). All samples were incubated for 1 hour prior to measuring the UV absorbance.

To further examine the specificity of the tyrosinase catalyzed reaction, and to examine the specificity of the chitosan adsorption step, spectrophotometry was used to measure UV-absorbance of the aqueous phase. Curve A of FIG. 11A shows the UV-absorbance of a solution of p-hydroxyphenoxyacetic acid. When mushroom tyrosinase was added to such a solution, Curve B of FIG. 11A shows a shift in wavelength and a large increase in the UV absorbance of the solution. This change in UV-absorbance is consistent with the conversion of a phenol to a quinone (Duckworth et al, 1970, *J. Biol. Chem.* 245:1613–1625) When p-hydroxyphenoxyacetic acid was contacted with both mushroom tyrosinase and chitosan, Curve C of FIG. 11A shows an almost complete reduction in UV-absorbing material. This reduction in UV-absorbance is consistent with previous studies in which it was shown that quinones, but not unreacted phenols, are strongly bound to chitosan (Sun et al, 1992, *Biotechnol. Progr.* 9: 179–186). Thus FIG. 11A supports the contention that the p-hydroxyphenoxyacetic acid can be effectively removed from solution by treatment with tyrosinase and chitosan.

Figure 11B:
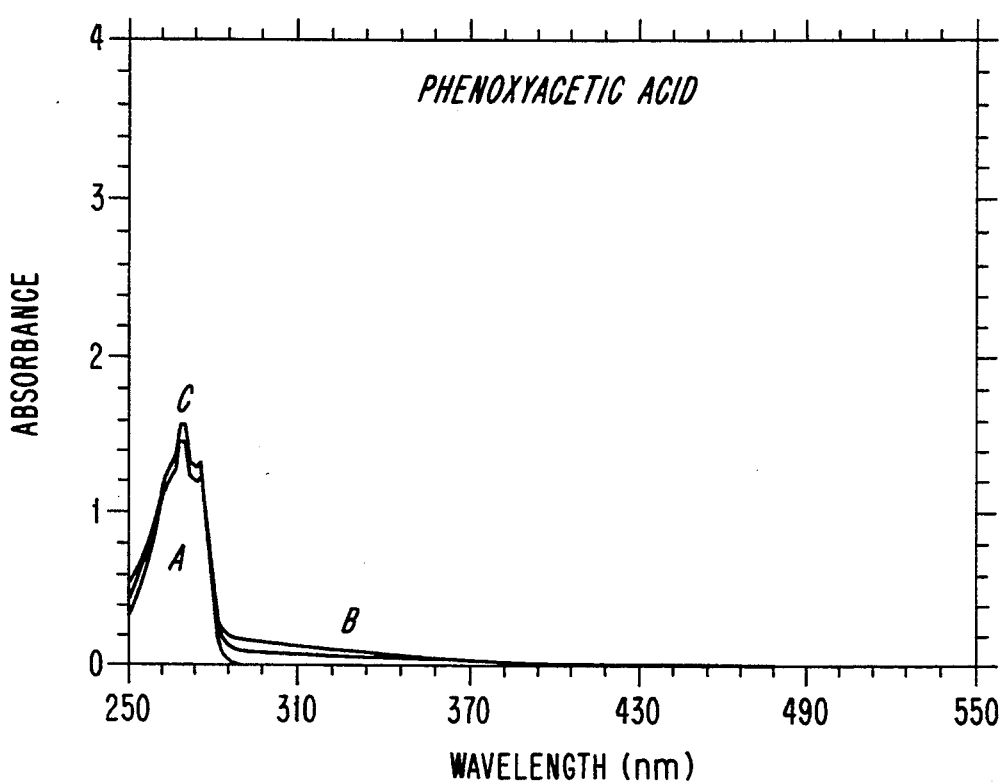

A similar experiment was conducted with phenoxyacetic acid. FIG. 11B shows that the UV absorbance of the phenoxyacetic acid solution is unaffected by the addition of tyrosinase (i.e. Curves A and B in FIG. 11B). This observation is consistent with those in FIG. 10 and supports the conclusion that tyrosinase is unable to react with the nonphenol, phenoxyacetic acid. When both mushroom tyrosinase and chitosan were added to a solution containing phenoxyacetic acid, the UV absorbance (Curve C of FIG. 11B) shows little, if any, change. This observation is again consistent with the conclusion that tyrosinase does not react with phenoxyacetic acid. Further, the observation that chitosan additions do not affect the UV absorbance of the remaining aqueous phase is consistent with the previously-reported conclusion that chitosan is unable to adsorb most organics (Payne et al, 1992, *Biotechnol. Bioeng.* 40:1011–1018; Sun et al, 1992, *Biotechnol. Progr.* 9:179–186). Thus the results in FIG. 11B show that phenoxyacetic acid is unaffected by the presence of tyrosinase and chitosan.

In the final experiment, a mixture of phenoxyacetic and p-hydroxyphenoxyacetic acids was examined to determine the separations capabilities of tyrosinase reaction/chitosan adsorption. Due to ambiguities associated with the tyrosinase reaction (i.e. various products including oligomeric phenols can be formed (Bollag, 1992, *Environ. Sci. Technol.* 26:1876–1881; Dawson et al, 1963, *Ann. NY Acad. Sci.* 100:937–950; Dec et al, 1990, *Arch. Environ. Contain. Toxicol.* 19:543–550; Mason et al, 1949, *J. Biol. Chem.* 180:235–247), the choice of analytical methods is important. For instance, although chromatographic techniques can readily detect the two phenoxyacetic acid compounds, it has been difficult to quantitatively follow the conversion to quinones and subsequent oligomeric phenols using chromatographic methods (Payne et al, 1992, *Biotechnol. Bioeng.* 40:10111018). To avoid such ambiguities, UV-visible spectrophotometry was used since all products from the tyrosinase-catalyzed reaction have high UV absorptivities. The UV absorbance of the control which contained only phenoxyacetic acid is shown in Curve A of FIG. 12. When a solution containing both phenoxyacetic and p-hydroxyphenoxyacetic acids was examined (Curve B of FIG. 12), the UV absorbance was observed to increase relative to the control due to the presence of the second solute. The addition of mushroom tyrosinase and chitosan to a mixture of phenoxyacetic and p-hydroxyphenoxyacetic acids resulted in a nearly complete elimination of the UV absorbance associated with the hydroxyphenoxyacetic acid (Curve C of FIG. 12). Thus the results in FIG. 12 indicate that the combination of tyrosinase reaction and chitosan adsorption resulted in the removal of the p-hydroxyphenoxyacetic acid while phenoxyacetic acid was completely retained in solution.

Figure 12:
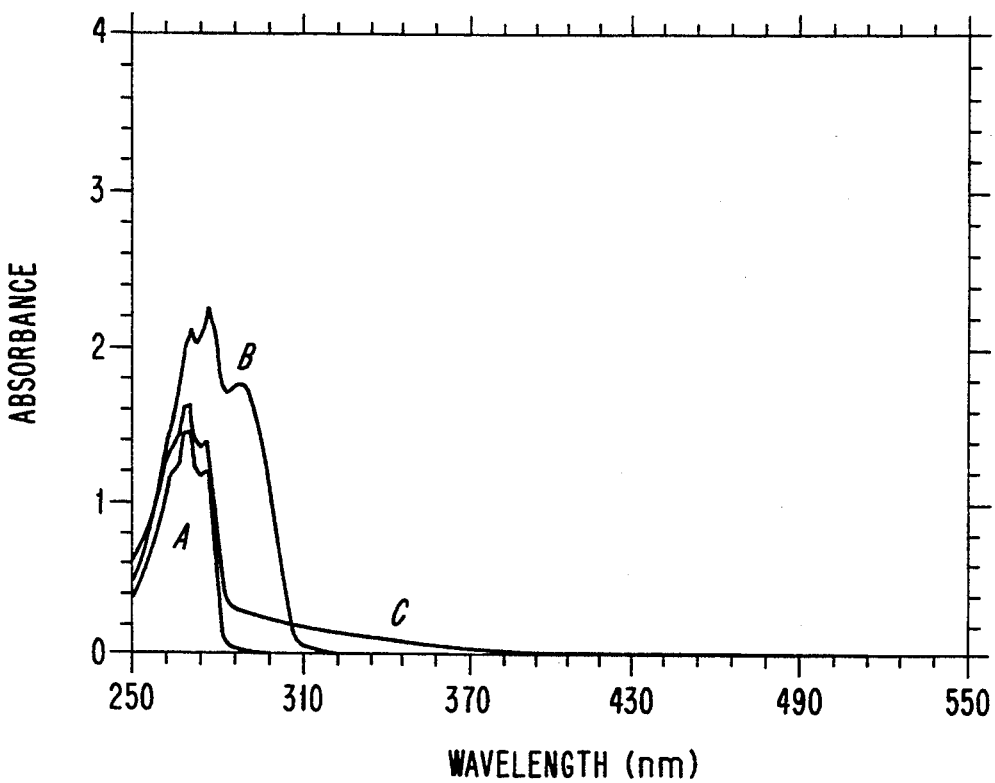
FIG. 12. Selectivity of tyrosinase reaction/chitosan adsorption for removing the hydroxyphenoxyacetic acid contaminant from a mixture containing the phenoxyacetic acid precursor. Curve A is the UV absorbance of a 1 mM phenoxyacetic acid solution. Curve B is the UV absorbance of the aqueous mixture containing both phenoxyacetic acid ( 1 mM) and p-hydroxyphenoxyacetic acid (0.7 mM). Curve C is the UV absorbance of the aqueous mixture after one hour incubation with mushroom tyrosinase (50 Units/mL) and chitosan (5 w/v %). The initial solute concentrations were chosen to permit sensitive analysis by UV absorbance.

In summary, FIG. 12 demonstrates that tyrosinase and chitosan can be used to selectively and efficiently remove the contaminant (p-hydroxyphenoxyacetic acid) from the penicillin V recycle stream. Because of the selectivity and efficiency of TR/CA, it is possible to envision the addition of tyrosinase and chitosan directly to a phenoxyacetic acid feed tank in a manner analogous to the use of a drying agent to eliminate water from a tank containing a non-aqueous solvent. Compared to alternative separation approaches such as liquid chromatography or solvent extraction, TR/CA would be simple to implement and would not require extracting or eluting solvents.

Example 5

Upgrading an Intermediate Process Stream: Aryl Ether Synthesis

Figure 14A:
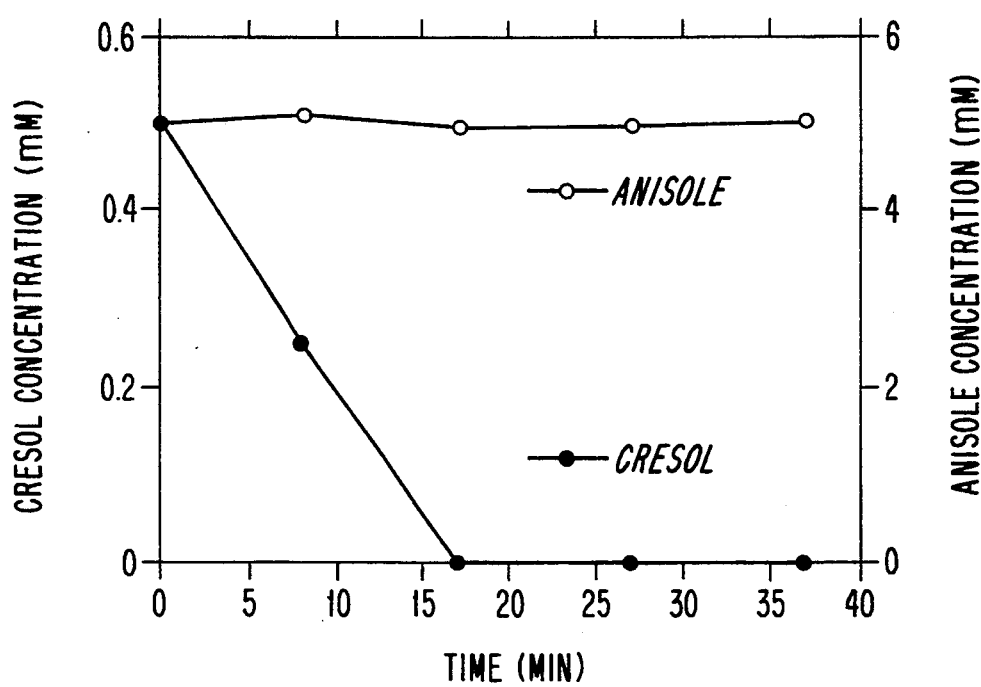
FIG. 14A. Gas chromatography (GC) shows that the addition of tyrosinase and chitosan results in the complete removal of the phenol (cresol) while the concentration of the ether anisole) is unaffected. In this experiment, mushroom tyrosinase (50 units/ml) was added to an aqueous mixture containing 0.5 mM of cresol and 5 mM anisole.
Figure 14B:
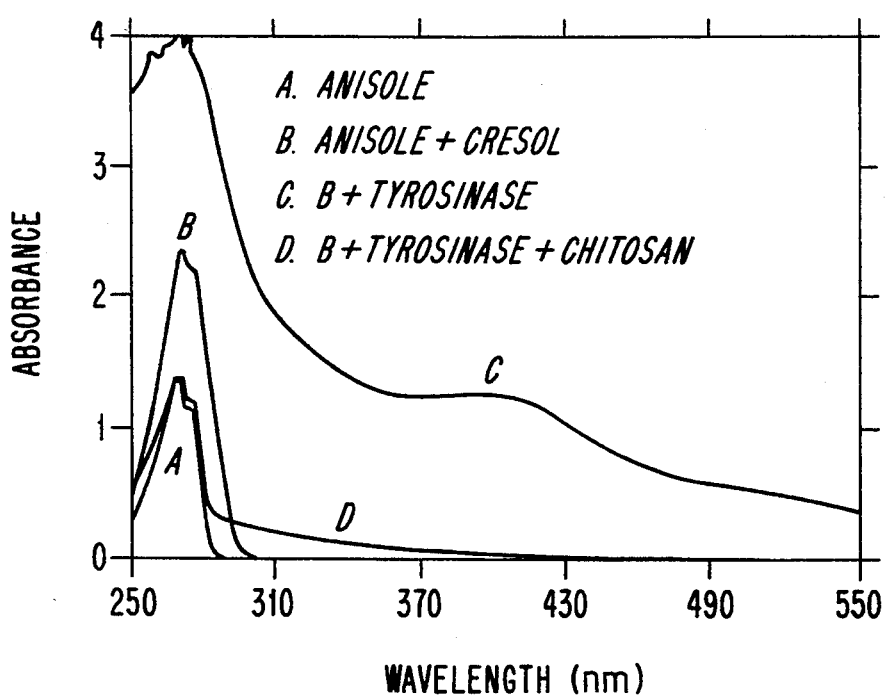
FIG. 14B. Ultraviolet/Visible (UV/Vis) spectrophotometry shows that UV-absorbing material resulting from the tyrosinase-catalyzed phenol oxidation is completely removed in the presence of chitosan. Curve A shows the absorbance of the control containing 2 mM anisole. Curve B shows the UV absorbance increases (as expected) when a solution containing both anisole (2mM) and cresol (1 mM) was scanned. Curve C shows that when mushroom tyrosinase (50 units/ml) was added to a solution containing both anisole and cresol, the absorbance was observed to markedly increase with a broad peak appearing near 400 nm. This 400 nm peak is characteristic of quirtones (Duckworth and Coleman, J. Biol. Chem. 245:1613–1625, 1970), while the large increase in absorbance at the higher wavelengths is commonly observed when oligomeric phenols are formed. The results in Curve C of FIG. 14B are expected if the cresol is converted by tyrosinase into a soluble quinone which subsequently forms oligomeric phenols. Curve D shows that when both tyrosinase and chitosan (5 %w/v) were added to the anisole-cresol mixture, the absorbance was markedly reduced compared to Curve C and approaches the absorbance of the anisole control of Curve A.

To demonstrate the capabilities of this enzymatic approach for selectively and efficiently removing a contaminating phenol from an aryl ether manufacturing stream (see FIG. 13), the experiments shown in FIG. 14 were conducted. FIG. 14(A) shows that when a mixture of cresol (the phenol) and anisole (the ether) were incubated with tyrosinase and chitosan, and when gas chromatography was used for analysis, the phenol was observed to be completely removed from solution, while the concentration of the ether was unaffected. Although the results in FIG. 14(A) support our conclusion that TR/CA selectively and efficiently removes the contaminating phenol without affecting the concentration of the desired ether, gas chromatographic analysis has serious limitations. Because the tyrosinase-generated o-quinones are unstable, numerous products have been observed for the tyrosinase-catalyzed reaction including dimeric and oligomeric phenols. Such products are often not readily observable—not to mention quantifiable—using GC. A more sensitive, although less quantitative, analytical approach involves the use of Ultraviolet/Visible (UV/Vis) spectrophotometry since all the products of the tyrosinase-catalyzed reaction are expected to have strong absorptivities. The UV/Vis scans shown in FIG. 14(B) demonstrate that when tyrosinase and chitosan were added to a mixture of cresol and anisole, the absorptivities associated with cresol (and its reaction products) were eliminated while the absorptivity associated with anisole was unaffected.

Thus, FIG. 14 demonstrates that in the presence of tyrosinase and chitosan, the concentration of the nonphenolic ether is not altered, while the contaminating phenol is completely convened and absorbed onto chitosan. These results illustrate the potential of this enzymatic approach for upgrading an intermediate process stream in the manufacture of aryl ethers.

Example 6

Improving Manufacturing Efficiencies: Vinyl Polymerization Processing

Figure 15:
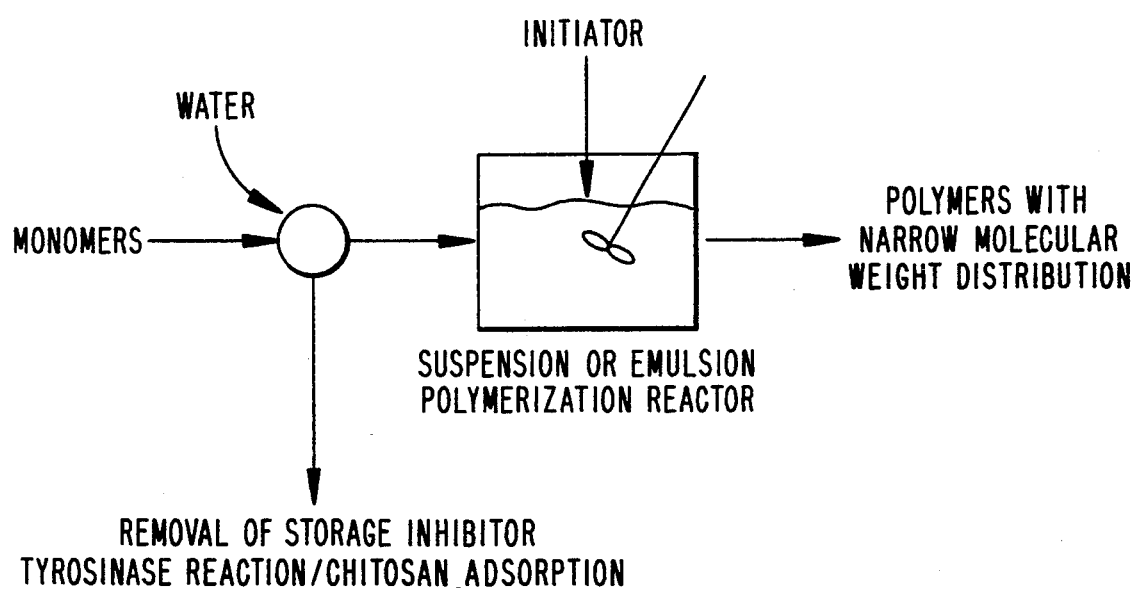
FIG. 15 is a schematic illustrating the need to selectively remove storage inhibitors to exert greater control in suspension and emulsion polymerization processes.
Figure 16A:
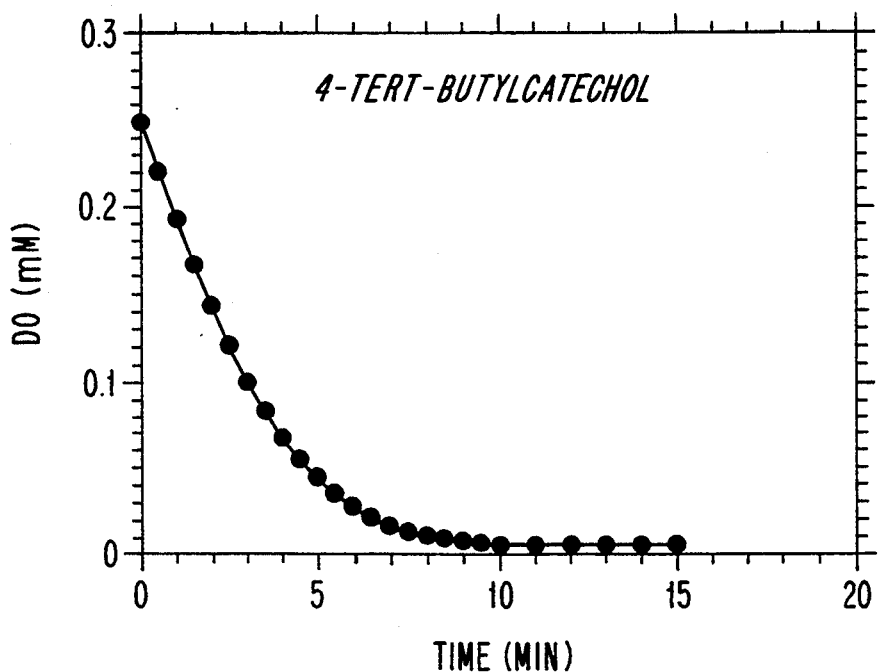
FIG. 16A. The consumption of dissolved oxygen shows that tyrosinase is capable of reacting with the tert-butylcatechol storage inhibitor. In this experiment, mushroom tyrosinase (20 units/ml) was added to solutions containing 0.5 mM of tert-butylcatechol.
Figure 16B:
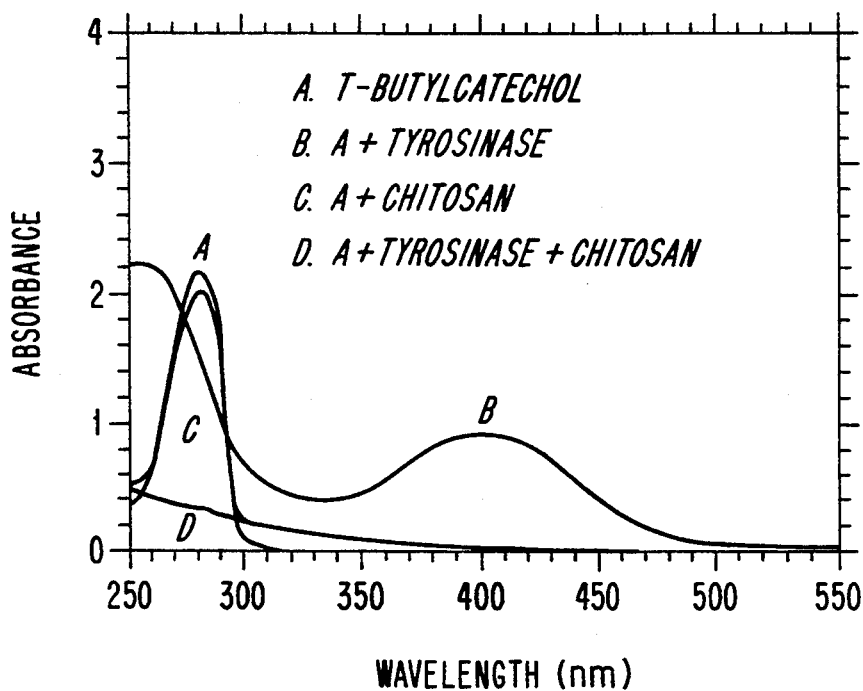
FIG. 16B UV/Vis spectrophotometry shows that the storage inhibitor (tert-butylcatechol) and its UV-absorbing oxidation products can be removed from aqueous solution. Curve A shows the UV absorbance of an aqueous solution of 0.6 mM tert-butylcatechol. Curve B shows the absorbance after adding 15 units/ml mushroom tyrosinase to the tert-butylcatechol solution. Curve C shows the absorbance after chitosan (5 w/v %) was added to the tert-butylcatechol solution. Curve D shows the absorbance after both tyrosinase and chitosan were added to the tert-butylcatechol solution. As can be seen, the tert-butylcatechol storage inhibitor: is unable to bind to chitosan by itself (Curves A and C are very similar); is converted by tyrosinase to what appears to be a quinone (Curve B); and is completely removed from solution by the combination of tyrosinase and chitosan (Curve D).

Because the major storage inhibitors are phenols (tert-butylcatechol, hydroquinone and p-methoxyphenol) we have begun to investigate whether TR/CA can be utilized to efficiently remove such inhibitors (see FIG. 15). These results are shown in FIG. 16. Based on oxygen consumption measurements, FIG. 16(A) shows that tyrosinase is capable of catalyzing the oxidation of tert-butylcatechol. FIG. 16(B) shows UV/Vis scans which demonstrate that tert-butylcatechol is efficiently removed from solution by the combination of tyrosinase reaction and chitosan adsorption.

Thus FIG. 16 shows that TR/CA can remove tert-butylcatechol from aqueous solution and thus may offer an opportunity for efficiently removing storage inhibitors for emulsion and suspension polymerizations. It is currently believed that an effective method for inhibitor removal would allow the development of more efficient polymerization processes with a corresponding reduction in the amount of waste resulting from the formation of inappropriately sized polymer.

Although the present invention has been described with reference to the presently preferred embodiment, it should be understood that the skilled artisan may make various modifications, substitutions, omissions, and changes without departing from the spirit of the invention. Accordingly, it is intended that the scope of the present invention be limited only by the scope of the following claims, including equivalents thereof.

We claim:

1. A two-step method for the selective removal of a phenolic compound from a mixture of compounds, comprising:
   a) enzymatically converting said phenolic compound with tyrosinas to a converted compound adsorbable by a chitosan sorbent; and
   b) adsorbing said converted compound to a chitosan sorbent to selectively remove said converted compound from said mixture.

2. The method of claim 3, wherein the phenolic compound is converted to a quinone.

3. The method of claim 6, wherein the chitosan sorbent has essentially no binding affinity for a phenolic compound.

4. A method for the selective removal of a phenolic contaminant from complex mixtures, comprising:
   (a) oxidizing the phenolic contaminant with a tyrosinase enzyme specific for the contaminant; and (b) binding the oxidized contaminant to a chitosan sorbent.

5. The method of claim 4, wherein the phenolic contaminant is converted to a quinone.

6. The method of claim 4, wherein the chitosan sorbent has essentially no binding affinity for a phenolic compound.

7. A method for removing a phenolic contaminant from a recycle stream comprising:
   a) oxidizing said phenolic contaminant with an oxidizing enzyme comprising tyrosinase, which enzyme is specific for said phenolic contaminant; and
   b) binding said oxidized contaminant to a chitosan sorbent.

8. The method of claim 7, wherein the phenolic compound is converted to a quinone.

9. The method of claim 7, wherein the sorbent has essentially no binding affinity for a phenolic compound.

10. The method of claim 7, wherein the recycle stream is used for producing an antibiotic.

11. The method of claim 10, wherein the antibiotic is penicillin V.

12. The method of claim 11, wherein the contaminant is a hydroxylated phenoxyacetic acid formed from hydroxylation of a phenoxyacetic acid precursor by a penicillin producing culture.

13. The method of claim 1, wherein the phenolic compound is cresol.

14. The method of claim 13, wherein the mixture is an aryl ether manufacturing stream.

15. The method of claim 13, wherein the cresol is converted to a quinone.

16. The method of claim 13, wherein the chitosan sorbent has essentially no binding affinity for cresol.

17. A method of improving the manufacturing efficiency of a polymer, comprising:
   a) enzymatically converting a polymerization-inhibiting phenolic compound present in a solution of monomers to a converted compound adsorbable by a chitosan sorbent; and
   b) adsorbing said converted compound to a chitosan sorbent to selectively remove said converted compound from said mixture.

18. The method of claim 17, wherein the phenolic compound is convened to a quinone.

19. The method of claim 18, wherein the phenolic compound is tertbutylcatechol, hydroquinone or p-methoxyphenol.

20. The method of claim 17, wherein the chitosan sorbent has essentially no binding affinity for a phenolic compound.

* * * * *